US010570378B2

(12) United States Patent
Ji et al.

(10) Patent No.: US 10,570,378 B2
(45) Date of Patent: Feb. 25, 2020

(54) TARGETED HISTONE ACETYLATION

(71) Applicant: SIGMA-ALDRICH CO. LLC, St. Louis, MO (US)

(72) Inventors: Qingzhou Ji, St. Louis, MO (US); Carol Kreader, St. Louis, MO (US)

(73) Assignee: Sigma-Aldrich Co. LLC, St. Louis, MO (US)

(*) Notice: Subject to any disclaimer, the term of this patent is extended or adjusted under 35 U.S.C. 154(b) by 0 days.

(21) Appl. No.: 14/381,381

(22) PCT Filed: Feb. 28, 2013

(86) PCT No.: PCT/US2013/028322
§ 371 (c)(1),
(2) Date: Aug. 27, 2014

(87) PCT Pub. No.: WO2013/130807
PCT Pub. Date: Sep. 6, 2013

(65) Prior Publication Data
US 2015/0079657 A1 Mar. 19, 2015

Related U.S. Application Data

(60) Provisional application No. 61/604,350, filed on Feb. 28, 2012.

(51) Int. Cl.
C12N 9/10 (2006.01)
C07K 14/47 (2006.01)
C12N 15/62 (2006.01)

(52) U.S. Cl.
CPC ............ C12N 9/1029 (2013.01); C07K 14/47 (2013.01); C12Y 203/01048 (2013.01); C07K 2319/09 (2013.01); C07K 2319/81 (2013.01)

(58) Field of Classification Search
None
See application file for complete search history.

(56) References Cited

U.S. PATENT DOCUMENTS

| 5,789,538 | A | 8/1998 | Rebar et al. |
| 5,925,523 | A | 7/1999 | Dove et al. |
| 6,007,988 | A | 12/1999 | Choo et al. |
| 6,013,453 | A | 1/2000 | Choo et al. |
| 6,140,466 | A | 10/2000 | Barbas, III et al. |
| 6,200,759 | B1 | 3/2001 | Dove et al. |
| 6,242,568 | B1 | 6/2001 | Barbas, III et al. |
| 6,410,248 | B1 | 6/2002 | Greisman et al. |
| 6,453,242 | B1 | 9/2002 | Eisenberg et al. |
| 6,479,626 | B1 | 11/2002 | Kim et al. |
| 6,534,261 | B1 | 3/2003 | Cox, III et al. |
| 6,903,185 | B2 | 6/2005 | Kim et al. |
| 6,919,204 | B2 | 7/2005 | Wolffe et al. |
| 7,001,768 | B2 | 2/2006 | Wolffe |
| 7,153,949 | B2 | 12/2006 | Kim et al. |
| 7,652,036 | B2 * | 1/2010 | Finn .................. C07D 215/12 514/311 |
| 2006/0003416 | A1 * | 1/2006 | Otte .................. C12N 15/63 435/69.1 |
| 2006/0123506 | A1 * | 6/2006 | Hannoufa ............ C07K 14/415 800/278 |
| 2006/0251642 | A1 | 11/2006 | Wolffe et al. |
| 2009/0023153 | A1 | 1/2009 | Wolffe et al. |
| 2010/0323424 | A1 | 12/2010 | Wolffe et al. |

FOREIGN PATENT DOCUMENTS

| WO | 98/37186 A1 | 8/1998 |
| WO | 98/53057 A1 | 11/1998 |
| WO | 00/27878 A1 | 5/2000 |
| WO | 01/83793 A2 | 11/2001 |
| WO | 01/88197 A2 | 11/2001 |
| WO | 02/077227 A2 | 10/2002 |
| WO | 03/027247 A2 | 4/2003 |
| WO | 2004/056986 A2 | 7/2004 |
| WO | 2005/028630 A2 | 3/2005 |
| WO | 2006/094106 | 9/2006 |
| WO | 2010/056808 | 5/2010 |
| WO | 2013/130807 A1 | 9/2013 |

OTHER PUBLICATIONS

Dawson et al. Science (1999) 285, 245-248.*
Ogryzko et al. (1996) Cell 87, 953-959.*
Thompson, P.R., et al. 2004 Nature Structural & Molecular Biology 11(4): 308-315.*
Beerli et al., "Engineering polydactyl zinc-finger transcription factors", Nature Biotechnology, 2002, pp. 135-141, vol. 20.
Choo et al., "Advances in zinc finger engineering", Current Opinion in Structural Biology, 2000, pp. 411-416, vol. 10.
Doyon et al., "Heritable Targeted Gene Disruption in Zebrafish Using Designed Zinc Finger Nucleases", Nature Biotechnology, 2008, pp. 702-708, vol. 26, No. 6.
International Search Report and Written Opinion from related International Application No. PCT/US2013/028322, dated May 13, 2013; 10 pgs.
Isalan et al., "A rapid, generally applicable method to engineer zinc fingers illustrated by targeting the HIV-1 promoter", Nature Biotechnology, 2001, pp. 656-660, vol. 19, No. 7.
Li et al., "Chimeric DNA methyltransferases target DNA methylation to specific DNA sequences and repress expression of target genes", Nucleic Acids Research, 2007, pp. 100-112, vol. 35, No. 1.
Lombardo et al., "Gene editing in human stem cells using zinc finger nucleases and integrase-defective lentiviral vector delivery", Nature Biotechnology, 2007, pp. 1298-1306, vol. 25, No. 11.
Makkerh et al., "Comparative mutagenesis of nuclear localization signals reveals the importance of neutral and acidic amino acids", Current Biology, 1996, pp. 1025-1027, vol. 6, No. 8.

(Continued)

Primary Examiner — Marsha Tsay
(74) Attorney, Agent, or Firm — Daniel S. Kasten

(57) ABSTRACT

The present disclosure provides compositions and methods for acetylating histones at targeted chromosomal locations in a cell. In particular, the disclosure provides a fusion protein comprising a DNA binding domain and at least one histone acetyltransferase (HAT) domain, such that the DNA binding domain targets the fusion protein to a targeted chromosomal location and the HAT domain acetylates histones at the targeted location.

4 Claims, 12 Drawing Sheets

Specification includes a Sequence Listing.

(56) References Cited

OTHER PUBLICATIONS

Mandell et al., "Zinc Finger Tools: custom DNA-binding domains for transcription factors and nucleases", Nucleic Acids Research, 2006, pp. W516-W523, vol. 34.

Meister et al., "Heterodimeric DNA methyltransferases as a platform for creating designer zinc finger methyltransferases for targeted DNA methylation in cells", Nucleic Acids Research, 2010, pp. 1749-1759, vol. 38, No. 5.

Minczuk et al., "Sequence-specific modification of mitochondrial DNA using a chimeric zinc finger methylase", PNAS, 2006, pp. 19689-19694, vol. 103, No. 52.

Moehle et al., "Targeted gene addition into a specified location in the human genome using designed zinc finger nucleases", PNAS, 2007, pp. 3055-3060, vol. 104, No. 9.

Nomura et al., "In Vivo Site-Specific DNA Methylation with a Designed Sequence-Enabled DNA Methylase", Journal of the American Chemical Society, 2007, pp. 8676-8677, vol. 129, No. 28.

Pabo et al., "Design and Selection of Novel Cys2 His2 Zinc Finger Proteins", Annu. Rev. Biochem., 2001, pp. 313-340, vol. 70.

Sander et al., "Zinc Finger Targeter (ZiFiT): an engineered zinc finger/target site design tool", Nucleic Acids Research, 2007, pp. W599-W605, vol. 35, Web Server issue.

Santiago et al., "Targeted gene knockout in mammalian cells by using engineered zinc-finger nucleases", PNAS, 2008, pp. 5809-5814, vol. 105, No. 15.

Segal et al., "Custom DNA-binding proteins come of age: polydactyl zinc-finger proteins", Current Opinion in Biotechnology, 2001, pp. 632-637, vol. 12.

Sera et al., "Rational Design of Artificial Zinc-Finger Proteins Using a Nondegenerate Recognition Code Table", Biochemistry, 2002, pp. 7074-7081, vol. 41.

Snowden et al., "Gene-Specific Targeting of H3K9 Methylation Is Sufficient for Initiating Repression In Vivo", Current Biology, 2002, pp. 2159-2166, vol. 12, No. 2.

Uniprot Q09472 Histone acetyltransferase p. 300 (EP300_Human), Feb. 22, 2012; 12 pgs.

Urnov et al., "Highly efficient endogenous human gene correction using designed zinc-finger nucleases", Nature, 2005, pp. 646-651, vol. 435.

Xu et al., "Cytosine methylation targetted to pre-determined sequences", Nature Genetics, 1997, pp. 376-378, vol. 17. No. 4.

Zhang et al., "Synthetic Zinc Finger Transcription Factor Action at an Endogenous Chromosomal Site: Activation of The Human Erythropoietin Gene", The Journal of Biological Chemistry, 2000, pp. 33850-33860, vol. 275, No. 43.

European Search Report from related European Application No. 13754523.2, dated Feb. 2, 2016, 12 pgs.

\* cited by examiner

SEQUENCE LISTING

<160> NUMBER OF SEQ ID NOS: 13

<210> SEQ ID NO 1
<211> LENGTH: 19
<212> TYPE: DNA
<213> ORGANISM: Homo sapiens

<400> SEQUENCE: 1
ggagggccag gaatcgggc                                                19

<210> SEQ ID NO 2
<211> LENGTH: 184
<212> TYPE: PRT
<213> ORGANISM: Artificial Sequence
<220> FEATURE:
<223> OTHER INFORMATION: SYNTHESIZED

<400> SEQUENCE: 2

Ala Ala Met Ala Glu Arg Pro Phe Gln Cys Arg Ile Cys Met Arg Asn
1               5                   10                  15

Phe Ser Asp Arg Ser His Leu Thr Arg His Ile Arg Thr His Thr Gly
            20                  25                  30

Glu Lys Pro Phe Ala Cys Asp Ile Cys Gly Arg Lys Phe Ala Arg Asn
        35                  40                  45

Asp Asp Arg Lys Lys His Thr Lys Ile His Thr Gly Ser Gln Lys Pro
    50                  55                  60

Phe Gln Cys Arg Ile Cys Met Arg Asn Phe Ser Gln Ser Gly Asn Leu
65                  70                  75                  80

Ala Arg His Ile Arg Thr His Thr Gly Glu Lys Pro Phe Ala Cys Asp
                85                  90                  95

Ile Cys Gly Arg Lys Phe Ala Ala Lys Trp Asn Leu Asp Ala His Thr
            100                 105                 110

Lys Ile His Thr His Pro Arg Ala Pro Ile Pro Lys Pro Phe Gln Cys
        115                 120                 125

Arg Ile Cys Met Arg Asn Phe Ser Arg Ser Ala His Leu Ser Arg His
    130                 135                 140

Ile Arg Thr His Thr Gly Glu Lys Pro Phe Ala Cys Asp Ile Cys Gly
145                 150                 155                 160

```
Arg Lys Phe Ala Gln Ser Gly His Leu Ser Arg His Thr Lys Ile His
            165                 170                 175
Leu Arg Gln Lys Asp Ala Ala Arg
        180
```

<210> SEQ ID NO 3
<211> LENGTH: 21
<212> TYPE: DNA
<213> ORGANISM: Artificial Sequence
<220> FEATURE:
<223> OTHER INFORMATION: SYNTHESIZED

<400> SEQUENCE: 3
gaagatgggg tgaaatttgg c       21

<210> SEQ ID NO 4
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 4
tggcactctc tcaggctctg          20

<210> SEQ ID NO 5
<211> LENGTH: 19
<212> TYPE: DNA
<213> ORGANISM: Artificial Sequence
<220> FEATURE:
<223> OTHER INFORMATION: SYTHESIZED

<400> SEQUENCE: 5
cggcttggag acctctcag           19

<210> SEQ ID NO 6
<211> LENGTH: 18
<212> TYPE: DNA
<213> ORGANISM: Artificial Sequence
<220> FEATURE:
<223> OTHER INFORMATION: SYTHESIZED

<400> SEQUENCE: 6
ccagcttcac ggcaccag            18

<210> SEQ ID NO 7
<211> LENGTH: 19
<212> TYPE: DNA
<213> ORGANISM: Homo sapiens

<400> SEQUENCE: 7
ggatggtggt gcagcagtg           19

<210> SEQ ID NO 8
<211> LENGTH: 183
<212> TYPE: PRT
<213> ORGANISM: Artificial Sequence
<220> FEATURE:
<223> OTHER INFORMATION: SYTHESIZED

<400> SEQUENCE: 8

```
Ala Ala Met Ala Glu Arg Pro Phe Gln Cys Arg Ile Cys Met Arg Asn
 1               5                  10                  15
Phe Ser Arg Ser Asp Ala Leu Ser Arg His Ile Arg Thr His Thr Gly
            20                  25                  30
```

Glu Lys Pro Phe Ala Cys Asp Ile Cys Gly Arg Lys Phe Ala Gln Ser
            35                  40                  45

Gly Asp Leu Thr Arg His Thr Lys Ile His Thr Gly Gly Gln Arg Pro
        50                  55                  60

Phe Gln Cys Arg Ile Cys Met Arg Asn Phe Ser Gln Ser Gly Asp Leu
65                  70                  75                  80

Thr Arg His Ile Arg Thr His Thr Gly Glu Lys Pro Phe Ala Cys Asp
                85                  90                  95

Ile Cys Gly Arg Lys Phe Ala Thr Ser Gly His Leu Ser Arg His Thr
                100                 105                 110

Lys Ile His Thr Gly Gly Gly Ser Gln Lys Pro Phe Gln Cys Arg
                115                 120                 125

Ile Cys Met Arg Asn Phe Ser Arg Ser Asp His Leu Ser Asn His Ile
                130                 135                 140

Arg Thr His Thr Gly Glu Lys Pro Phe Ala Cys Asp Ile Cys Gly Lys
145                 150                 155                 160

Lys Phe Ala Gln Ser Ala Thr Arg Ile Thr His Thr Lys Ile His Leu
                    165                 170                 175

Arg Gln Lys Asp Ala Ala Arg
            180

<210> SEQ ID NO 9
<211> LENGTH: 180
<212> TYPE: PRT
<213> ORGANISM: Artificial Sequence
<220> FEATURE:
<223> OTHER INFORMATION: SYNTHESIZED

<400> SEQUENCE: 9

Ala Ala Met Ala Glu Arg Pro Phe Gln Cys Arg Ile Cys Met Arg Asn
1               5                   10                  15

Phe Ser Arg Ser Ala His Leu Ser Arg His Ile Arg Thr His Thr Gly
                20                  25                  30

Glu Lys Pro Phe Ala Cys Asp Ile Cys Gly Arg Lys Phe Ala Arg Ser
            35                  40                  45

Asp Ala Leu Ala Arg His Thr Lys Ile His Thr Gly Ser Gln Lys Pro
        50                  55                  60

Phe Gln Cys Arg Ile Cys Met Arg Asn Phe Ser Asp Arg Ser His Leu
65                  70                  75                  80

Thr Arg His Ile Arg Thr His Thr Gly Glu Lys Pro Phe Ala Cys Asp
                85                  90                  95

Ile Cys Gly Arg Lys Phe Ala Thr Ser Gly Ser Leu Thr Arg His Thr
                100                 105                 110

Lys Ile His Thr Gly Ser Gln Lys Pro Phe Gln Cys Arg Ile Cys Met
                115                 120                 125

Arg Asn Phe Ser Arg Ser Asp Asn Leu Ser Thr His Ile Arg Thr His
                130                 135                 140

Thr Gly Glu Lys Pro Phe Ala Cys Asp Ile Cys Gly Arg Lys Phe Ala
145                 150                 155                 160

Asp Asn Arg Asp Arg Ile Lys His Thr Lys Ile His Leu Arg Gln Lys
                165                 170                 175

Asp Ala Ala Arg
            180

<210> SEQ ID NO 10

<211> LENGTH: 180
<212> TYPE: PRT
<213> ORGANISM: Artificial Sequence
<220> FEATURE:
<223> OTHER INFORMATION: SYNTHESIZED

<400> SEQUENCE: 10

Ala Ala Met Ala Glu Arg Pro Phe Gln Cys Arg Ile Cys Met Arg Asn
1               5                   10                  15

Phe Ser Gln Ser Ser Asn Leu Ala Arg His Ile Arg Thr His Thr Gly
            20                  25                  30

Glu Lys Pro Phe Ala Cys Asp Ile Cys Gly Arg Lys Phe Ala Gln Ser
        35                  40                  45

Gly His Leu Ser Arg His Thr Lys Ile His Thr Gly Ser Gln Lys Pro
    50                  55                  60

Phe Gln Cys Arg Ile Cys Met Arg Asn Phe Ser Gln Ser Ser Asn Leu
65                  70                  75                  80

Ala Arg His Ile Arg Thr His Thr Gly Glu Lys Pro Phe Ala Cys Asp
                85                  90                  95

Ile Cys Gly Arg Lys Phe Ala Gln Ser Gly His Leu Ser Arg His Thr
            100                 105                 110

Lys Ile His Thr Gly Ser Gln Lys Pro Phe Gln Cys Arg Ile Cys Met
        115                 120                 125

Arg Asn Phe Ser Gln Ser Ser Asp Leu Ser Arg His Ile Arg Thr His
    130                 135                 140

Thr Gly Glu Lys Pro Phe Ala Cys Asp Ile Cys Gly Arg Lys Phe Ala
145                 150                 155                 160

Gln Ser Gly Asn Leu Ala Arg His Thr Lys Ile His Leu Arg Gln Lys
                165                 170                 175

Asp Ala Ala Arg
            180

<210> SEQ ID NO 11
<211> LENGTH: 180
<212> TYPE: PRT
<213> ORGANISM: Artificial Sequence
<220> FEATURE:
<223> OTHER INFORMATION: SYNTHESIZED

<400> SEQUENCE: 11

Ala Ala Met Ala Glu Arg Pro Phe Gln Cys Arg Ile Cys Met Arg Asn
1               5                   10                  15

Phe Ser Arg Ser Asp Asp Leu Ser Lys His Ile Arg Thr His Thr Gly
            20                  25                  30

Glu Lys Pro Phe Ala Cys Asp Ile Cys Gly Arg Lys Phe Ala Asp Arg
        35                  40                  45

Ser His Leu Ala Arg His Thr Lys Ile His Thr Gly Ser Gln Lys Pro
    50                  55                  60

Phe Gln Cys Arg Ile Cys Met Arg Asn Phe Ser Gln Ser Gly Asp Leu
65                  70                  75                  80

Thr Arg His Ile Arg Thr His Thr Gly Glu Lys Pro Phe Ala Cys Asp
                85                  90                  95

Ile Cys Gly Arg Lys Phe Ala Arg Ser Asp Asp Leu Thr Arg His Thr
            100                 105                 110

Lys Ile His Thr Gly Ser Gln Lys Pro Phe Gln Cys Arg Ile Cys Met
        115                 120                 125

Arg Asn Phe Ser Arg Ser Asp Asp Leu Thr Arg His Ile Arg Thr His

```
                        130                 135                 140

Thr Gly Glu Lys Pro Phe Ala Cys Asp Ile Cys Gly Arg Lys Phe Ala
145                 150                 155                 160

Arg Asn Asp Asp Arg Lys His Thr Lys Ile His Leu Arg Gln Lys
                165                 170                 175

Asp Ala Ala Arg
            180

<210> SEQ ID NO 12
<211> LENGTH: 180
<212> TYPE: PRT
<213> ORGANISM: Artificial Sequence
<220> FEATURE:
<223> OTHER INFORMATION: SYNTHESIZED

<400> SEQUENCE: 12

Ala Ala Met Ala Glu Arg Pro Phe Gln Cys Arg Ile Cys Met Arg Asn
1               5                   10                  15

Phe Ser Arg Ser Ala Asp Leu Thr Arg His Ile Arg Thr His Thr Gly
            20                  25                  30

Glu Lys Pro Phe Ala Cys Asp Ile Cys Gly Arg Lys Phe Ala Arg Ser
        35                  40                  45

Asp Asp Arg Lys Thr His Thr Lys Ile His Thr Gly Ser Gln Lys Pro
    50                  55                  60

Phe Gln Cys Arg Ile Cys Met Arg Asn Phe Ser Asp Arg Ser His Leu
65                  70                  75                  80

Thr Arg His Ile Arg Thr His Thr Gly Glu Lys Pro Phe Ala Cys Asp
                85                  90                  95

Ile Cys Gly Arg Lys Phe Ala Arg Ser Asp Leu Thr Arg His Thr
            100                 105                 110

Lys Ile His Thr Gly Ser Gln Lys Pro Phe Gln Cys Arg Ile Cys Met
        115                 120                 125

Arg Asn Phe Ser Gln Ser Ser Asp Leu Ser Arg His Ile Arg Thr His
    130                 135                 140

Thr Gly Glu Lys Pro Phe Ala Cys Asp Ile Cys Gly Arg Lys Phe Ala
145                 150                 155                 160

Tyr His Trp Tyr Leu Lys Lys His Thr Lys Ile His Leu Arg Gln Lys
                165                 170                 175

Asp Ala Ala Arg
            180

<210> SEQ ID NO 13
<211> LENGTH: 2414
<212> TYPE: PRT
<213> ORGANISM: Homo sapiens

<400> SEQUENCE: 13

Met Ala Glu Asn Val Val Glu Pro Gly Pro Pro Ser Ala Lys Arg Pro
1               5                   10                  15

Lys Leu Ser Ser Pro Ala Leu Ser Ala Ser Ala Ser Asp Gly Thr Asp
            20                  25                  30

Phe Gly Ser Leu Phe Asp Leu Glu His Asp Leu Pro Asp Glu Leu Ile
        35                  40                  45

Asn Ser Thr Glu Leu Gly Leu Thr Asn Gly Gly Asp Ile Asn Gln Leu
    50                  55                  60

Gln Thr Ser Leu Gly Met Val Gln Asp Ala Ala Ser Lys His Lys Gln
65                  70                  75                  80
```

```
Leu Ser Glu Leu Leu Arg Ser Gly Ser Ser Pro Asn Leu Asn Met Gly
                85                  90                  95

Val Gly Gly Pro Gly Gln Val Met Ala Ser Gln Ala Gln Gln Ser Ser
            100                 105                 110

Pro Gly Leu Gly Leu Ile Asn Ser Met Val Lys Ser Pro Met Thr Gln
            115                 120                 125

Ala Gly Leu Thr Ser Pro Asn Met Gly Met Gly Thr Ser Gly Pro Asn
130                 135                 140

Gln Gly Pro Thr Gln Ser Thr Gly Met Met Asn Ser Pro Val Asn Gln
145                 150                 155                 160

Pro Ala Met Gly Met Asn Thr Gly Met Asn Ala Gly Met Asn Pro Gly
                165                 170                 175

Met Leu Ala Ala Gly Asn Gly Gln Gly Ile Met Pro Asn Gln Val Met
            180                 185                 190

Asn Gly Ser Ile Gly Ala Gly Arg Gly Arg Gln Asn Met Gln Tyr Pro
            195                 200                 205

Asn Pro Gly Met Gly Ser Ala Gly Asn Leu Leu Thr Glu Pro Leu Gln
        210                 215                 220

Gln Gly Ser Pro Gln Met Gly Gly Gln Thr Gly Leu Arg Gly Pro Gln
225                 230                 235                 240

Pro Leu Lys Met Gly Met Met Asn Asn Pro Asn Pro Tyr Gly Ser Pro
                245                 250                 255

Tyr Thr Gln Asn Pro Gly Gln Gln Ile Gly Ala Ser Gly Leu Gly Leu
            260                 265                 270

Gln Ile Gln Thr Lys Thr Val Leu Ser Asn Asn Leu Ser Pro Phe Ala
        275                 280                 285

Met Asp Lys Lys Ala Val Pro Gly Gly Met Pro Asn Met Gly Gln
            290                 295                 300

Gln Pro Ala Pro Gln Val Gln Gln Pro Gly Leu Val Thr Pro Val Ala
305                 310                 315                 320

Gln Gly Met Gly Ser Gly Ala His Thr Ala Asp Pro Glu Lys Arg Lys
                325                 330                 335

Leu Ile Gln Gln Gln Leu Val Leu Leu Leu His Ala His Lys Cys Gln
            340                 345                 350

Arg Arg Glu Gln Ala Asn Gly Glu Val Arg Gln Cys Asn Leu Pro His
        355                 360                 365

Cys Arg Thr Met Lys Asn Val Leu Asn His Met Thr His Cys Gln Ser
370                 375                 380

Gly Lys Ser Cys Gln Val Ala His Cys Ala Ser Ser Arg Gln Ile Ile
385                 390                 395                 400

Ser His Trp Lys Asn Cys Thr Arg His Asp Cys Pro Val Cys Leu Pro
                405                 410                 415

Leu Lys Asn Ala Gly Asp Lys Arg Asn Gln Gln Pro Ile Leu Thr Gly
            420                 425                 430

Ala Pro Val Gly Leu Gly Asn Pro Ser Ser Leu Gly Val Gly Gln Gln
        435                 440                 445

Ser Ala Pro Asn Leu Ser Thr Val Ser Gln Ile Asp Pro Ser Ser Ile
450                 455                 460

Glu Arg Ala Tyr Ala Ala Leu Gly Leu Pro Tyr Gln Val Asn Gln Met
465                 470                 475                 480

Pro Thr Gln Pro Gln Val Gln Ala Lys Asn Gln Gln Asn Gln Gln Pro
                485                 490                 495
```

-continued

Gly Gln Ser Pro Gln Gly Met Arg Pro Met Ser Asn Met Ser Ala Ser
              500                 505                 510

Pro Met Gly Val Asn Gly Val Gly Val Gln Thr Pro Ser Leu Leu
              515                 520                 525

Ser Asp Ser Met Leu His Ser Ala Ile Asn Ser Gln Asn Pro Met Met
              530                 535                 540

Ser Glu Asn Ala Ser Val Pro Ser Leu Gly Pro Met Pro Thr Ala Ala
545                 550                 555                 560

Gln Pro Ser Thr Thr Gly Ile Arg Lys Gln Trp His Glu Asp Ile Thr
              565                 570                 575

Gln Asp Leu Arg Asn His Leu Val His Lys Leu Val Gln Ala Ile Phe
              580                 585                 590

Pro Thr Pro Asp Pro Ala Ala Leu Lys Asp Arg Arg Met Glu Asn Leu
              595                 600                 605

Val Ala Tyr Ala Arg Lys Val Glu Gly Asp Met Tyr Glu Ser Ala Asn
610                 615                 620

Asn Arg Ala Glu Tyr Tyr His Leu Leu Ala Glu Lys Ile Tyr Lys Ile
625                 630                 635                 640

Gln Lys Glu Leu Glu Glu Lys Arg Arg Thr Arg Leu Gln Lys Gln Asn
              645                 650                 655

Met Leu Pro Asn Ala Ala Gly Met Val Pro Val Ser Met Asn Pro Gly
              660                 665                 670

Pro Asn Met Gly Gln Pro Gln Pro Gly Met Thr Ser Asn Gly Pro Leu
              675                 680                 685

Pro Asp Pro Ser Met Ile Arg Gly Ser Val Pro Asn Gln Met Met Pro
              690                 695                 700

Arg Ile Thr Pro Gln Ser Gly Leu Asn Gln Phe Gly Gln Met Ser Met
705                 710                 715                 720

Ala Gln Pro Pro Ile Val Pro Arg Gln Thr Pro Leu Gln His His
              725                 730                 735

Gly Gln Leu Ala Gln Pro Gly Ala Leu Asn Pro Pro Met Gly Tyr Gly
              740                 745                 750

Pro Arg Met Gln Gln Pro Ser Asn Gln Gly Gln Phe Leu Pro Gln Thr
              755                 760                 765

Gln Phe Pro Ser Gln Gly Met Asn Val Thr Asn Ile Pro Leu Ala Pro
              770                 775                 780

Ser Ser Gly Gln Ala Pro Val Ser Gln Ala Gln Met Ser Ser Ser Ser
785                 790                 795                 800

Cys Pro Val Asn Ser Pro Ile Met Pro Pro Gly Ser Gln Gly Ser His
              805                 810                 815

Ile His Cys Pro Gln Leu Pro Gln Pro Ala Leu His Gln Asn Ser Pro
              820                 825                 830

Ser Pro Val Pro Ser Arg Thr Pro Thr Pro His His Thr Pro Pro Ser
              835                 840                 845

Ile Gly Ala Gln Gln Pro Pro Ala Thr Thr Ile Pro Ala Pro Val Pro
              850                 855                 860

Thr Pro Pro Ala Met Pro Pro Gly Pro Gln Ser Gln Ala Leu His Pro
865                 870                 875                 880

Pro Pro Arg Gln Thr Pro Thr Pro Thr Thr Gln Leu Pro Gln Gln
              885                 890                 895

Val Gln Pro Ser Leu Pro Ala Ala Pro Ser Ala Asp Gln Pro Gln Gln
              900                 905                 910

Gln Pro Arg Ser Gln Gln Ser Thr Ala Ala Ser Val Pro Thr Pro Thr

```
                    915                 920                 925
Ala Pro Leu Leu Pro Pro Gln Pro Ala Thr Pro Leu Ser Gln Pro Ala
    930                 935                 940
Val Ser Ile Glu Gly Gln Val Ser Asn Pro Ser Thr Ser Ser Thr
945                 950                 955                 960
Glu Val Asn Ser Gln Ala Ile Ala Glu Lys Gln Pro Ser Gln Glu Val
                965                 970                 975
Lys Met Glu Ala Lys Met Glu Val Asp Gln Pro Glu Pro Ala Asp Thr
            980                 985                 990
Gln Pro Glu Asp Ile Ser Glu Ser Lys Val Glu Asp Cys Lys Met Glu
        995                 1000                1005
Ser Thr Glu Thr Glu Glu Arg Ser Thr Glu Leu Lys Thr Glu Ile
    1010                1015                1020
Lys Glu Glu Glu Asp Gln Pro Ser Thr Ser Ala Thr Gln Ser Ser
    1025                1030                1035
Pro Ala Pro Gly Gln Ser Lys Lys Ile Phe Lys Pro Glu Glu
    1040                1045                1050
Leu Arg Gln Ala Leu Met Pro Thr Leu Glu Ala Leu Tyr Arg Gln
    1055                1060                1065
Asp Pro Glu Ser Leu Pro Phe Arg Gln Pro Val Asp Pro Gln Leu
    1070                1075                1080
Leu Gly Ile Pro Asp Tyr Phe Asp Ile Val Lys Ser Pro Met Asp
    1085                1090                1095
Leu Ser Thr Ile Lys Arg Lys Leu Asp Thr Gly Gln Tyr Gln Glu
    1100                1105                1110
Pro Trp Gln Tyr Val Asp Asp Ile Trp Leu Met Phe Asn Asn Ala
    1115                1120                1125
Trp Leu Tyr Asn Arg Lys Thr Ser Arg Val Tyr Lys Tyr Cys Ser
    1130                1135                1140
Lys Leu Ser Glu Val Phe Glu Gln Glu Ile Asp Pro Val Met Gln
    1145                1150                1155
Ser Leu Gly Tyr Cys Cys Gly Arg Lys Leu Glu Phe Ser Pro Gln
    1160                1165                1170
Thr Leu Cys Cys Tyr Gly Lys Gln Leu Cys Thr Ile Pro Arg Asp
    1175                1180                1185
Ala Thr Tyr Tyr Ser Tyr Gln Asn Arg Tyr His Phe Cys Glu Lys
    1190                1195                1200
Cys Phe Asn Glu Ile Gln Gly Glu Ser Val Ser Leu Gly Asp Asp
    1205                1210                1215
Pro Ser Gln Pro Gln Thr Thr Ile Asn Lys Glu Gln Phe Ser Lys
    1220                1225                1230
Arg Lys Asn Asp Thr Leu Asp Pro Glu Leu Phe Val Glu Cys Thr
    1235                1240                1245
Glu Cys Gly Arg Lys Met His Gln Ile Cys Val Leu His His Glu
    1250                1255                1260
Ile Ile Trp Pro Ala Gly Phe Val Cys Asp Gly Cys Leu Lys Lys
    1265                1270                1275
Ser Ala Arg Thr Arg Lys Glu Asn Lys Phe Ser Ala Lys Arg Leu
    1280                1285                1290
Pro Ser Thr Arg Leu Gly Thr Phe Leu Glu Asn Arg Val Asn Asp
    1295                1300                1305
Phe Leu Arg Arg Gln Asn His Pro Glu Ser Gly Glu Val Thr Val
    1310                1315                1320
```

```
Arg Val Val His Ala Ser Asp Lys Thr Val Glu Val Lys Pro Gly
1325                1330                1335

Met Lys Ala Arg Phe Val Asp Ser Gly Glu Met Ala Glu Ser Phe
1340                1345                1350

Pro Tyr Arg Thr Lys Ala Leu Phe Ala Phe Glu Glu Ile Asp Gly
1355                1360                1365

Val Asp Leu Cys Phe Phe Gly Met His Val Gln Glu Tyr Gly Ser
1370                1375                1380

Asp Cys Pro Pro Pro Asn Gln Arg Arg Val Tyr Ile Ser Tyr Leu
1385                1390                1395

Asp Ser Val His Phe Phe Arg Pro Lys Cys Leu Arg Thr Ala Val
1400                1405                1410

Tyr His Glu Ile Leu Ile Gly Tyr Leu Glu Tyr Val Lys Lys Leu
1415                1420                1425

Gly Tyr Thr Thr Gly His Ile Trp Ala Cys Pro Pro Ser Glu Gly
1430                1435                1440

Asp Asp Tyr Ile Phe His Cys His Pro Pro Asp Gln Lys Ile Pro
1445                1450                1455

Lys Pro Lys Arg Leu Gln Glu Trp Tyr Lys Lys Met Leu Asp Lys
1460                1465                1470

Ala Val Ser Glu Arg Ile Val His Asp Tyr Lys Asp Ile Phe Lys
1475                1480                1485

Gln Ala Thr Glu Asp Arg Leu Thr Ser Ala Lys Glu Leu Pro Tyr
1490                1495                1500

Phe Glu Gly Asp Phe Trp Pro Asn Val Leu Glu Glu Ser Ile Lys
1505                1510                1515

Glu Leu Glu Gln Glu Glu Glu Arg Lys Arg Glu Glu Asn Thr
1520                1525                1530

Ser Asn Glu Ser Thr Asp Val Thr Lys Gly Asp Ser Lys Asn Ala
1535                1540                1545

Lys Lys Lys Asn Asn Lys Lys Thr Ser Lys Asn Lys Ser Ser Leu
1550                1555                1560

Ser Arg Gly Asn Lys Lys Pro Gly Met Pro Asn Val Ser Asn
1565                1570                1575

Asp Leu Ser Gln Lys Leu Tyr Ala Thr Met Glu Lys His Lys Glu
1580                1585                1590

Val Phe Phe Val Ile Arg Leu Ile Ala Gly Pro Ala Ala Asn Ser
1595                1600                1605

Leu Pro Pro Ile Val Asp Pro Asp Pro Leu Ile Pro Cys Asp Leu
1610                1615                1620

Met Asp Gly Arg Asp Ala Phe Leu Thr Leu Ala Arg Asp Lys His
1625                1630                1635

Leu Glu Phe Ser Ser Leu Arg Arg Ala Gln Trp Ser Thr Met Cys
1640                1645                1650

Met Leu Val Glu Leu His Thr Gln Ser Gln Asp Arg Phe Val Tyr
1655                1660                1665

Thr Cys Asn Glu Cys Lys His His Val Glu Thr Arg Trp His Cys
1670                1675                1680

Thr Val Cys Glu Asp Tyr Asp Leu Cys Ile Thr Cys Tyr Asn Thr
1685                1690                1695

Lys Asn His Asp His Lys Met Glu Lys Leu Gly Leu Gly Leu Asp
1700                1705                1710
```

```
Asp Glu Ser Asn Asn Gln Gln Ala Ala Thr Gln Ser Pro Gly
    1715                1720            1725

Asp Ser Arg Arg Leu Ser Ile Gln Arg Cys Ile Gln Ser Leu Val
    1730                1735            1740

His Ala Cys Gln Cys Arg Asn Ala Asn Cys Ser Leu Pro Ser Cys
    1745                1750            1755

Gln Lys Met Lys Arg Val Val Gln His Thr Lys Gly Cys Lys Arg
    1760                1765            1770

Lys Thr Asn Gly Gly Cys Pro Ile Cys Lys Gln Leu Ile Ala Leu
    1775                1780            1785

Cys Cys Tyr His Ala Lys His Cys Gln Glu Asn Lys Cys Pro Val
    1790                1795            1800

Pro Phe Cys Leu Asn Ile Lys Gln Lys Leu Arg Gln Gln Gln Leu
    1805                1810            1815

Gln His Arg Leu Gln Gln Ala Gln Met Leu Arg Arg Arg Met Ala
    1820                1825            1830

Ser Met Gln Arg Thr Gly Val Val Gly Gln Gln Gly Leu Pro
    1835                1840            1845

Ser Pro Thr Pro Ala Thr Pro Thr Thr Pro Thr Gly Gln Gln Pro
    1850                1855            1860

Thr Thr Pro Gln Thr Pro Gln Pro Thr Ser Gln Pro Gln Pro Thr
    1865                1870            1875

Pro Pro Asn Ser Met Pro Pro Tyr Leu Pro Arg Thr Gln Ala Ala
    1880                1885            1890

Gly Pro Val Ser Gln Gly Lys Ala Ala Gly Gln Val Thr Pro Pro
    1895                1900            1905

Thr Pro Pro Gln Thr Ala Gln Pro Pro Leu Pro Gly Pro Pro Pro
    1910                1915            1920

Ala Ala Val Glu Met Ala Met Gln Ile Gln Arg Ala Ala Glu Thr
    1925                1930            1935

Gln Arg Gln Met Ala His Val Gln Ile Phe Gln Arg Pro Ile Gln
    1940                1945            1950

His Gln Met Pro Pro Met Thr Pro Met Ala Pro Met Gly Met Asn
    1955                1960            1965

Pro Pro Pro Met Thr Arg Gly Pro Ser Gly His Leu Glu Pro Gly
    1970                1975            1980

Met Gly Pro Thr Gly Met Gln Gln Gln Pro Pro Trp Ser Gln Gly
    1985                1990            1995

Gly Leu Pro Gln Pro Gln Gln Leu Gln Ser Gly Met Pro Arg Pro
    2000                2005            2010

Ala Met Met Ser Val Ala Gln His Gly Gln Pro Leu Asn Met Ala
    2015                2020            2025

Pro Gln Pro Gly Leu Gly Gln Val Gly Ile Ser Pro Leu Lys Pro
    2030                2035            2040

Gly Thr Val Ser Gln Gln Ala Leu Gln Asn Leu Leu Arg Thr Leu
    2045                2050            2055

Arg Ser Pro Ser Ser Pro Leu Gln Gln Gln Gln Val Leu Ser Ile
    2060                2065            2070

Leu His Ala Asn Pro Gln Leu Leu Ala Ala Phe Ile Lys Gln Arg
    2075                2080            2085

Ala Ala Lys Tyr Ala Asn Ser Asn Pro Gln Pro Ile Pro Gly Gln
    2090                2095            2100

Pro Gly Met Pro Gln Gly Gln Pro Gly Leu Gln Pro Pro Thr Met
```

-continued

```
                2105                2110                2115
Pro Gly Gln Gln Gly Val His Ser Asn Pro Ala Met Gln Asn Met
    2120                2125                2130
Asn Pro Met Gln Ala Gly Val Gln Arg Ala Gly Leu Pro Gln Gln
    2135                2140                2145
Gln Pro Gln Gln Gln Leu Gln Pro Pro Met Gly Gly Met Ser Pro
    2150                2155                2160
Gln Ala Gln Gln Met Asn Met Asn His Asn Thr Met Pro Ser Gln
    2165                2170                2175
Phe Arg Asp Ile Leu Arg Arg Gln Gln Met Met Gln Gln Gln Gln
    2180                2185                2190
Gln Gln Gly Ala Gly Pro Gly Ile Gly Pro Gly Met Ala Asn His
    2195                2200                2205
Asn Gln Phe Gln Gln Pro Gln Gly Val Gly Tyr Pro Pro Gln Gln
    2210                2215                2220
Gln Gln Arg Met Gln His His Met Gln Gln Met Gln Gln Gly Asn
    2225                2230                2235
Met Gly Gln Ile Gly Gln Leu Pro Gln Ala Leu Gly Ala Glu Ala
    2240                2245                2250
Gly Ala Ser Leu Gln Ala Tyr Gln Gln Arg Leu Leu Gln Gln Gln
    2255                2260                2265
Met Gly Ser Pro Val Gln Pro Asn Pro Met Ser Pro Gln Gln His
    2270                2275                2280
Met Leu Pro Asn Gln Ala Gln Ser Pro His Leu Gln Gly Gln Gln
    2285                2290                2295
Ile Pro Asn Ser Leu Ser Asn Gln Val Arg Ser Pro Gln Pro Val
    2300                2305                2310
Pro Ser Pro Arg Pro Gln Ser Gln Pro Pro His Ser Ser Pro Ser
    2315                2320                2325
Pro Arg Met Gln Pro Gln Pro Ser Pro His His Val Ser Pro Gln
    2330                2335                2340
Thr Ser Ser Pro His Pro Gly Leu Val Ala Ala Gln Ala Asn Pro
    2345                2350                2355
Met Glu Gln Gly His Phe Ala Ser Pro Asp Gln Asn Ser Met Leu
    2360                2365                2370
Ser Gln Leu Ala Ser Asn Pro Gly Met Ala Asn Leu His Gly Ala
    2375                2380                2385
Ser Ala Thr Asp Leu Gly Leu Ser Thr Asp Asn Ser Asp Leu Asn
    2390                2395                2400
Ser Asn Leu Ser Gln Ser Thr Leu Asp Ile His
    2405                2410
```

TARGETED HISTONE ACETYLATION

CROSS-REFERENCE TO RELATED APPLICATIONS

This application is a U.S. National Stage Application of PCT International Application No. PCT/US2013/028322, filed Feb. 28, 2013, which claims the priority of U.S. Provisional Application No. 61/604,350, filed Feb. 28, 2012, the contents of each is hereby incorporated by reference in its entirety.

FIELD OF THE INVENTION

The present disclosure generally relates to means for acetylating histone proteins at targeted chromosomal locations.

BACKGROUND OF THE INVENTION

It is well established that histone acetylation is associated with transcriptional activity in eukaryotic cells. Acetylated core histones are known to preferentially associate with transcriptionally active chromatin. Acetylation occurs at lysine residues on the amino-terminal tails of histone proteins, thereby neutralizing the positive charge of the histone tails and decreasing their affinity for DNA. As a consequence, histone acetylation alters nucleosomal conformation, thereby increasing the accessibility of transcriptional regulatory proteins to chromatin templates.

Despite advances in identifying the large number of proteins having histone acetyltransferase or histone deacetylase activity and deciphering their roles in regulating gene expression, there is currently no way of modifying histone acetylation at specific locations. Although sodium butyrate is used to inhibit histone deacetylase activity, thereby indirectly increasing histone acetylation, this method of histone acetylation is global and non-specific. Acetylation, at essentially all locations, is modified. A need exists, therefore, for targeted histone acetylation. In particular, there is a need for means to target histone acetylase activity to specific chromosomal sequences such that histone proteins associated with the chromosomal sequence of interest can be acetylated.

SUMMARY OF THE INVENTION

The present disclosure, therefore, provides means for acetylating histone proteins at targeted chromosomal locations. One aspect of the present disclosure provides a fusion protein comprising a DNA binding domain and at least one p300 histone acetyltransferase (HAT) domain. In one embodiment, the DNA binding domain is a transcriptional activator-like effector DNA binding domain. In another embodiment, the DNA binding domain is a zinc finger DNA binding domain. In one embodiment, the zinc finger DNA binding domain comprises from about five to about seven zinc fingers. In a further embodiment, the HAT domain is derived from a mammalian p300 protein. In certain embodiments, the fusion protein further comprises at least one nuclear localization signal, at least one cell-penetrating domain, at least one marker domain, or combinations thereof. In one embodiment, the DNA binding domain of the fusion protein is an engineered zinc finger DNA binding domain comprising from about five to about seven zinc fingers and the HAT domain of the fusion protein is derived from a human p300 protein. In one embodiment, the engineered zinc finger DNA binding domain of the fusion protein binds a specific sequence located upstream or downstream of the transcriptional start site of chromosomal sequences encoding Oct4, Sox2, or PEDF.

The present disclosure also provides isolated nucleic acids encoding the fusion proteins disclosed herein.

A further aspect of the present disclosure provides a method for acetylating at least one histone protein at a targeted chromosomal location in a cell. The method comprises contacting the cell with a fusion protein or a nucleic acid encoding the fusion protein, wherein the fusion protein comprises a DNA binding domain and at least one p300 histone acetyltransferase (HAT) domain. Upon binding of the DNA binding domain to a sequence at the targeted chromosomal location, the p300 HAT domain acetylates at least one histone protein at the targeted chromosomal location. In one embodiment, the fusion protein acetylates histone H2A, histone H2B, histone H3, and/or histone H4. In specific exemplary embodiments, the fusion protein acetylates lysine 18 of histone H3 and/or lysine 27 of histone H3. In a further embodiment, a gene located near the targeted chromosomal sequence has increased levels of transcription. In various embodiments, the cell used in the method is a human cell, a mammalian cell, a non-mammalian vertebrate cell, an invertebrate cell, a stem cell, an embryo, or a single-cell eukaryote. In an exemplary embodiment, the cell is a human cell. In another embodiment, the DNA binding domain of the fusion protein is an engineered zinc finger DNA binding domain comprising from about five to about seven zinc fingers and the HAT domain of the fusion protein is derived from a human p300 protein. In another embodiment, the engineered zinc finger DNA binding domain of the fusion protein binds a specific sequence located upstream or downstream of the transcriptional start site of chromosomal sequences encoding Oct4, Sox2, or PEDF.

Other aspects and iterations of the disclosure are described in more detail below.

DETAILED DESCRIPTION OF THE INVENTION

Figure 1:
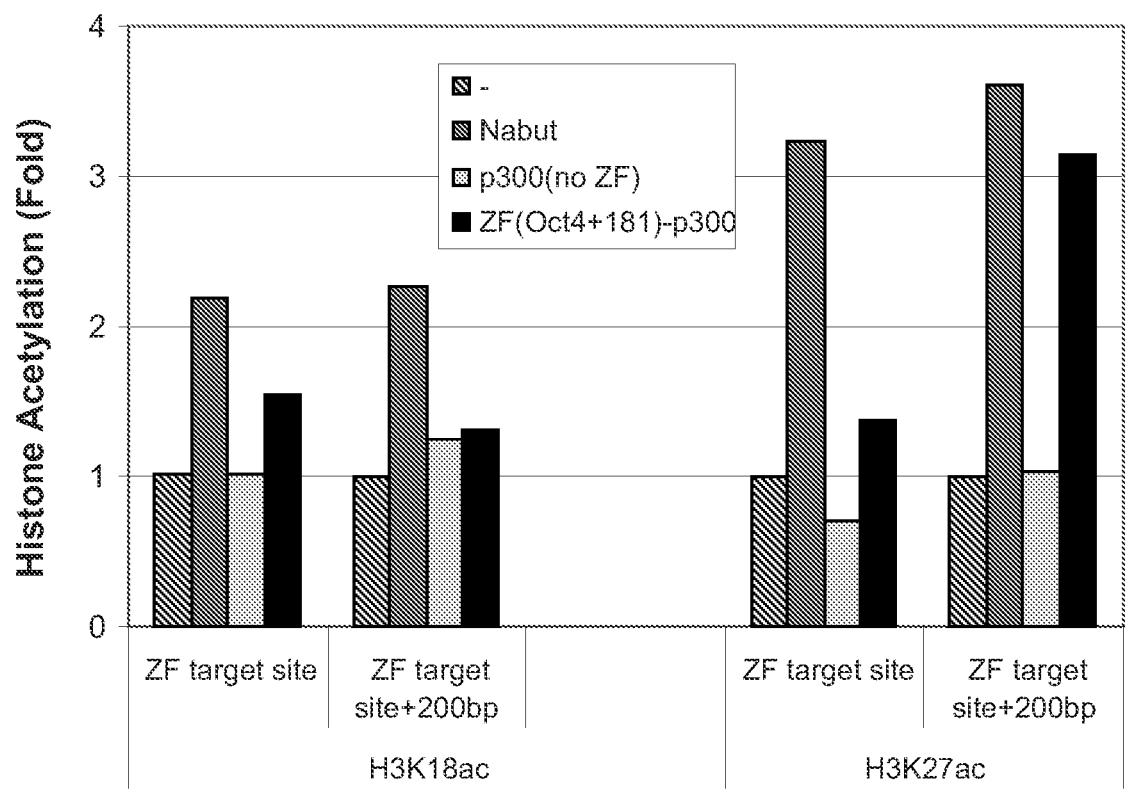
FIG. 1 illustrates targeted histone acetylation in HEK293 cells by the fusion protein ZF(Oct4+181)-p300. Plotted is the fold increase in acetylation at H3K18 and H3K27 at the target site and the target site+200 bp under the indicated treatment conditions. The zinc finger DNA binding domain ZF(Oct4+181) targets a sequence at +181 bp downstream of the transcriptional start site of OCT4. Cells treated with sodium butyrate (Nabut), a histone deacetylase inhibitor, were used as positive controls. Cells transfected with p300 HAT domain (without ZF domain) or GFP were used as negative controls.

The present disclosure provides means for acetylating histone and other proteins at specific chromosomal locations. In particular, the disclosure provides fusion proteins comprising a DNA binding domain and at least one histone acetyltransferase (HAT) domain that exhibits histone acetylase activity. The DNA binding domain is able to recognize and bind a specific sequence in a chromosomal sequence of interest, and the HAT domain is able to acetylate the lysine residues of histone or other chromosomal proteins. Accordingly, the fusion proteins disclosed herein can be used to acetylate proteins associated with the specific sequence targeted by the DNA binding domain. Targeted protein acetylation may be used to regulate the transcriptional activity or other effects of chromosomal protein acetylation at chromosomal sequences of interest.

(I) Fusion Protein

One aspect of the present disclosure provides a fusion protein comprising a DNA binding domain and at least one histone acetyltransferase (HAT) domain. Because the DNA binding domain recognizes and binds a specific DNA sequence, it targets the fusion protein to the specific sequence in a cellular chromosome. Upon binding to the specific sequence, the HAT domain of the fusion protein acetylates at least one protein associated with the specific sequence in the cellular chromosome.

(a) DNA Binding Domain

The fusion protein disclosed herein comprises a DNA binding domain, which contains at least one motif that recognizes and binds a specific sequence of DNA. The DNA binding domain can bind double-stranded DNA and/or single-stranded DNA. In general, the DNA binding domain recognizes and binds a specific sequence in the double-stranded DNA of a cellular chromosome.

A variety of DNA binding domains are suitable for inclusion in the fusion protein. Non-limiting examples of suitable DNA binding domains include AT hook domains, basic leucine zipper domains, beta-sheet domains, B3 domains, helix-loop-helix domains, helix-turn-helix domains, homeodomains, HMG box domains, immunoglobulin fold domains, leucine zipper domains, steroid receptor domains, transcription activator-like effector (TAL) effector domains, winged helix domains, winged helix turn helix domains, and zinc finger domains. The DNA binding domain can be derived from a naturally occurring protein. For example, the DNA binding domain can be derived from a naturally occurring transcription factor or DNA binding protein. Alternatively, the DNA binding domain can be an engineered or artificial polypeptide or protein.

(i) Zinc Finger DNA Binding Domains

In exemplary embodiments, the DNA binding domain is a zinc finger DNA binding domain. A zinc finger DNA binding domain comprises tandem repeats of two, three, or more zinc finger motifs (i.e., "zinc fingers"). Each zinc finger coordinates with zinc (or another ion) and interacts with about three consecutive nucleotide residues. A variety of zinc fingers are known, and can be classified by the type and order of these zinc coordinating residues (e.g., $Cys_2His_2$, $Cys_4$, and $Cys_6$).

Zinc finger DNA binding domains can be derived from naturally occurring proteins. Alternatively, zinc finger DNA binding domains can be engineered to recognize and bind to any nucleic acid sequence of choice. For example, arrays of engineered $Cys_2His_2$ zinc fingers are well known in the art. See, e.g., Beerli et al. (2002) Nat. Biotechnol. 20:135-141; Pabo et al. (2001) Ann. Rev. Biochem. 70:313-340; Isalan et al. (2001) Nat. Biotechnol. 19:656-660; Segal et al. (2001) Curr. Opin. Biotechnol. 12:632-637; Choo et al. (2000) Curr. Opin. Struct. Biol. 10:411-416; Zhang et al. (2000) J. Biol. Chem. 275(43):33850-33860; Doyon et al. (2008) Nat. Biotechnol. 26:702-708; and Santiago et al. (2008) Proc. Natl. Acad. Sci. USA 105:5809-5814.

An engineered zinc finger binding domain can have a novel binding specificity compared to a naturally-occurring zinc finger protein. Engineering methods include, but are not limited to, rational design and various types of selection. Rational design includes, for example, using databases comprising doublet, triplet, and/or quadruplet nucleotide sequences and individual zinc finger amino acid sequences, in which each doublet, triplet or quadruplet nucleotide sequence is associated with one or more amino acid sequences of zinc fingers which bind the particular triplet or quadruplet sequence. See, for example, U.S. Pat. Nos. 6,453,242 and 6,534,261, the disclosures of which are incorporated by reference herein in their entireties. As an example, the algorithm described in U.S. Pat. No. 6,453,242 can be used to design a zinc finger binding domain to target a preselected sequence. Alternative methods, such as rational design using a nondegenerate recognition code table can also be used to design a zinc finger binding domain to target a specific sequence (Sera et al. (2002) Biochemistry 41:7074-7081). Publically available web-based tools for identifying potential target sites in DNA sequences as well as designing zinc finger binding domains are known in the art. For example, tools for identifying potential target sites in DNA sequences can be found at zincfingertools.org. Tools for designing zinc finger binding domains can be found at zifit.partners.org/ZiFiT. (See also, Mandell et al. (2006) Nuc. Acid Res. 34:W516-W523; Sander et al. (2007) Nuc. Acid Res. 35:W599-W605.)

Exemplary methods of selecting a zinc finger recognition region include phage display and two-hybrid systems, and are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237, each of which is incorporated by reference herein in its entirety. In addition, enhancement of binding specificity for zinc finger binding domains has been described, for example, in WO 02/077227.

The zinc finger DNA binding domains designed for inclusion in the fusion proteins disclosed herein typically are engineered to recognize and bind a DNA sequence of at least about 12 nucleotides. In exemplary embodiments, the zinc finger DNA binding domains are engineered to recognize and bind a DNA sequence ranging from about 15 to about 21 nucleotides in length. Thus, the zinc finger DNA binding domains disclosed herein comprise at least four zinc fingers. In exemplary embodiments, the zinc finger DNA binding domain comprises from about 5 to about 7 zinc fingers. In one exemplary embodiment, the zinc finger DNA binding domain comprises five zinc fingers. In another exemplary embodiment, the zinc finger DNA binding domain comprises six zinc fingers. In still another exemplary embodiment, the zinc finger DNA binding domain comprises seven zinc fingers.

Zinc finger DNA binding domains and/or multi-fingered zinc finger proteins can be linked together using suitable linker sequences, including for example, linkers of five or more amino acids in length. See, U.S. Pat. Nos. 6,479,626; 6,903,185; and 7,153,949, the disclosures of which are incorporated by reference herein in their entireties, for non-limiting examples of linker sequences of six or more amino acids in length. The zinc finger DNA binding domains described herein can include a combination of suitable linkers between the individual zinc fingers of the protein.

(ii) TAL Effector DNA Binding Domains

In another embodiment, the DNA binding domain of the fusion protein is a TAL effector DNA binding domain. TAL effectors are transcription factors secreted by pathogenic bacteria when they infect various plant species. These proteins recognize plant DNA sequences through a central repeat domain consisting of a variable number of ~34 amino acid repeats, thereby activating the expression of plant genes that aid bacterial infection. The central repeat domain TAL effectors, therefore, is the DNA binding domain. There appears to be a simple one-to-one correspondence between the identity of two critical amino acids in each repeat and a specific nucleotide in the target DNA sequence. Thus, artificial TAL effector DNA binding domain can be engineered to recognize and bind any DNA sequence of interest. In general, TAL effector DNA binding domains designed for inclusion in the fusion proteins disclosed herein contain from about 2 to about 40 repeats. In specific embodiments, the TAL effector DNA binding domains contain from about 12 to about 25 repeats.

(iii) Specific DNA Binding Domains

In general, the DNA binding domain of the fusion protein is engineered to recognize and bind a specific sequence in a chromosomal sequence of interest. Non-limiting examples of suitable target sequences include those that encode reprogramming factors (e.g., Oct4, Sox2, Klf4, c-Myc, Nanog, Lin-28, miRNA 302-367 cluster, Zfp296, etc.), growth factors (e.g., Ang, BMPs, BDNF, EGF, FGF, GDNF, G-CSF, GDF9, HGF, HDGF, IGF, I-IGF 1, I-IGF 2, GDF8, NSF, NGF, PDGF, TGFs, TNF-α, VEGF, PEDF, PlGF, etc.), cytokines (e.g., interleukins, interferons, EPO, TPO, etc.), growth factor or cytokine receptors (e.g., FGFRs, NGFRs, HGFR, VEGFRs, EPOR, ErfBGFR, SCFR, TGFRs, BMPR, etc.), tumor suppressors (e.g., p53, p21, p16, VHL, CDH1, BRCA2, PTEN, VHL, APC, CD95, ST5, YPEL3, ST7, ST14, etc.), and cell cycle regulators (e.g., ANAPC2, ATR, AURKA, BCCIP, BCL2, BRCA2, CCNB1, CCNB2, CCNC, CCND1, CCND2, CCND3, CCNE1, CCNF, CCNH, CCNT1, CDC16, CDC20, CDC25C, CDC6, CDK1 (CDC2), CDK2, CDK4, CDK5R1, CDK6, CDK7, CDK8, CDKN1A (p21CIP1/WAF1), CDKN1B (p27KIP1), CKS1B, E2F1, E2F4, GADD45A, KNTC1, MKI67, RAD9A, RB1, SKP2, TFDP1, TFDP2, WEE1, etc.) activators/inhibitors, gene targets, etc.

The specific sequence that is recognized and bound by the DNA binding domain generally is located upstream or downstream of a transcriptional start site. For example, the specific sequence can be within several base pairs of the transcriptional start site or it can be located tens, hundreds, thousands, tens of thousands, or hundreds of thousands of base pairs upstream or downstream of the transcriptional start site. For example, the specific sequence may be located within about 1-100, 100-300, 300-1,000, 1,000-3,000, 3,000-10,000, 10,000-30,000, or 30,000-100,00 base pairs upstream or downstream of a transcriptional start site. In a further embodiment, the specific sequence can be located more than 100,000 base pairs upstream or downstream of a transcriptional start site.

In one exemplary embodiment, the DNA binding domain recognizes and binds a specific sequence located upstream or downstream of the transcriptional start site of the OCT4 gene. For example, the DNA binding domain can recognize and bind a specific sequence located from about −2000 base pair (bp) to about +3000 bp relative to the transcriptional start site of OCT4. In certain exemplary embodiments, the DNA binding domain can recognize and bind a specific sequence located from about −1700 base pair (bp) to about +1500 bp relative to the transcriptional start site of OCT4, including, for example, from about −100 bp to about +900 bp relative to the transcriptional start site of OCT4. In specific exemplary embodiments, the DNA binding domain recognizes and binds a specific sequence located at +181 bp, +286 bp, or +420 bp relative to the transcriptional start site of OCT4.

In another exemplary embodiment, the DNA binding domain recognizes and binds a specific sequence located upstream or downstream of the transcriptional start site of the PEDF gene. As an example, the DNA binding domain can recognize and bind a specific sequence located from about −1000 bp to about +2000 bp relative to the transcriptional start site of PEDF. In certain exemplary embodiments, the DNA binding domain can recognize and bind a specific sequence located from about −100 bp to about +500 bp relative to the transcriptional start site of PEDF. In one specific exemplary embodiment, the DNA binding domain recognizes and binds a specific sequence located at −92 bp relative to the transcriptional start site of PEDF.

In another exemplary embodiment, the DNA binding domain recognizes and binds a specific sequence located upstream or downstream of the transcriptional start site of the SOX2 gene. For example, the DNA binding domain can recognize and bind a specific sequence located from about −1000 bp to about +2000 bp relative to the transcriptional start site of SOX2. In certain exemplary embodiments, the DNA binding domain can recognize and bind a specific sequence located from about −100 bp to about +500 bp relative to the transcriptional start site of SOX2. In specific exemplary embodiments, the DNA binding domain recognizes and binds a specific sequence located at +185 bp or +475 bp relative to the transcriptional start site of SOX2.

(b) HAT Domain

The fusion protein disclosed herein also comprises at least one HAT domain. The HAT domain exhibits protein acetylase activity. For example the HAT domain can exhibit histone acetylase activity, i.e., it is able to acetylate lysine residues in histone proteins by transferring an acetyl group from acetyl CoA to form ε-N-acetyl lysine. Suitable histone proteins include the core histones, H2A, H2B, H3, and H4, and the linker histone, H1. The HAT domain can also exhibit acetylase activity to other chromosomally associated proteins. Chromosomally associated proteins include non-histone protein involved with chromatin structure, as well as enzymes and protein factors involved in transcription, replication, and other essential processes.

A variety of HAT domains are suitable for inclusion in the fusion protein. In embodiments in which the fusion protein comprises more than one HAT domain, the HAT domains may be the same or different. Non-limiting examples of suitable HAT domains are those derived from CREBBP (i.e., CREB-binding protein), CDY1, CDY2, CDYL1, CLOCK, ELP3, EP300 (i.e., E1A binding protein p300), ESA1, GCN5 (KAT2A), HAT1, KAT2B, KAT5, MYST1, MYST2, MYST3, MYST4, NCOA1, NCOA2, NCOA3, NCOAT, P/CAF, Tip60, TAFII250, or TF3C4. In one embodiment, the HAT domain is not SRC1 or a SRC1-related protein. In another embodiment, the HAT domain is not GCN5 (KAT2A). In an exemplary embodiment the HAT domain is derived from E1A binding protein p300, which is also known as p300, EP300, histone acetyltransferase p300, E1A-associated protein, or KAT3B.

The HAT domain can be of mammalian, vertebrate, invertebrate, or single-cell eukaryote origin. In some embodiments, the HAT domain is a p300 protein of mammalian origin. In exemplary embodiments, the Hat domain is a p300 protein of human origin. In one embodiment, the HAT domain ranges from about amino acid position 1000 to about amino acid position 2000 of the mammalian p300 protein. In another embodiment, the HAT domain ranges from about amino acid position 1100 to about amino acid position 1750 of a mammalian p300 protein. In a further embodiment, the HAT domain ranges from about amino acid position 1284 to about amino acid position 1673 of a mammalian p300 protein.

The HAT domain may be located N terminal or C terminal to the DNA binding domain. In embodiments in which more than one HAT domain is present, the HAT domains may be tandemly arranged, may flank the DNA binding domain, or any combination thereof. The HAT domain(s) and the DNA binding domain may be contiguous or they may be separated by a linker sequence or sequences. Suitable amino acid linker sequences are well known in the art.

(c) Optional Domains

In some embodiments, the fusion protein further comprises at least one nuclear localization signal or sequence (NLS). A NLS is an amino acid sequence which facilitates targeting the fusion protein into the nucleus where it mediates targeted histone acetylation. Nuclear localization signals are known in the art (e.g., see Makkerh et al. (1996) Current Biology 6:1025-1027). For example, the NLS can be derived from a naturally occurring protein such as SV40 T-antigen, nucleoplasmin, c-myc, hnRNPA1, Matα2, and so forth. Alternatively, the NLS can be a consensus sequence derived from a number of NLS sequences. The NLS can be located at the N-terminus, the C-terminal, or in an internal location of the fusion protein.

In additional embodiments, the fusion protein can also comprise at least one cell-penetrating domain. The cell-penetrating domain can be a cell-penetrating peptide sequence derived from HIV-1 TAT protein, a cell-penetrating peptide sequence derived from human hepatitis B virus, a cell penetrating peptide from Herpes simplex virus, MPG peptide, Pep-1 peptide, or a polyarginine peptide sequence. The cell-penetrating domain can be located at the N-terminus, the C-terminal, or in an internal location of the fusion protein.

In further embodiments, the fusion protein can comprise at least one marker domain. Suitable marker domains include fluorescent proteins, visible reporters, selectable markers, epitope tags, affinity tags, and the like. Non-limiting examples of suitable fluorescent proteins include green fluorescent proteins (e.g., GFP, GFP-2, tagGFP, turboGFP, EGFP, Emerald, Azami Green, Monomeric Azami Green, CopGFP, AceGFP, ZsGreen1), yellow fluorescent proteins (e.g. YFP, EYFP, Citrine, Venus, YPet, PhiYFP, ZsYellow1), blue fluorescent proteins (e.g. EBFP, EBFP2, Azurite, mKalaml, GFPuv, Sapphire, T-sapphire), cyan fluorescent proteins (e.g. ECFP, Cerulean, CyPet, AmCyanl, Midoriishi-Cyan), red fluorescent proteins (mKate, mKate2, mPlum, DsRed monomer, mCherry, mRFP1, DsRed-Express, DsRed2, DsRed-Monomer, HcRed-Tandem, HcRed1, AsRed2, eqFP611, mRasberry, mStrawberry, Jred), and orange fluorescent proteins (mOrange, mKO, Kusabira-Orange, Monomeric Kusabira-Orange, mTangerine, tdTomato) or any other suitable fluorescent protein. Non-limiting examples of visual reporters include luciferase, alkaline phosphatase, beta-galactosidase, beta-lactamase, horseradish peroxidase, and variants thereof. Examples of suitable selectable markers include, without limit, antibiotic selectable markers such as puromycin, zeomycin, neomycin, hydromycin, phleomycin, and the like. Suitable epitope tags include but are not limited to myc, AcV5, AU1, AU5, E, ECS, E2, FLAG, HA, Maltose binding protein, nus, Softag 1, Softag 3, Strep, SBP, Glu-Glu, HSV, KT3, S, 51, T7, V5, VSV-G, 6×His, BCCP, and calmodulin. Non-limiting examples of affinity tags include chitin binding protein (CBP), thioredoxin (TRX), poly(NANP), tandem affinity purification (TAP) tag, and glutathione-S-transferase (GST). The marker domain can be N terminal or C terminal to the DNA binding domain, the HAT domain(s), and/or additional domains.

(II) Nucleic Acid Encoding the Fusion Protein

Another aspect of the disclosure encompasses isolated nucleic acids encoding the fusion proteins described above in section (I). The nucleic acid encoding the fusion protein can be DNA, RNA, double-stranded, single-stranded, linear, or circular. In embodiments in which the nucleic acid is RNA, the RNA can be messenger RNA (mRNA). The mRNA can be 5' capped and/or 3' polyadenylated. The capping (or polyadenylation) can be performed during an in vitro synthesis reaction, or the capping (or polyadenylation) can be performed post-transcriptionally via a specific reaction.

The nucleic acid encoding the fusion protein can be operably linked to at least one promoter control sequence for expression in a cell of interest. In some embodiments, the nucleic acid is operably linked to a promoter control sequence for expression in a eukaryotic cell. The promoter control sequence can be constitutive or regulated (i.e., inducible or tissue-specific). Suitable constitutive promoter control sequences include, but are not limited to, cytomegalovirus immediate early promoter (CMV), simian virus (SV40) promoter, adenovirus major late promoter, Rous sarcoma virus (RSV) promoter, mouse mammary tumor virus (MMTV) promoter, phosphoglycerate kinase (PGK) promoter, elongation factor (ED1)-alpha promoter, ubiquitin promoters, actin promoters, tubulin promoters, immunoglobulin promoters, fragments thereof, or combinations of any of the foregoing. Non-limiting examples of suitable inducible promoter control sequences include those regulated by antibiotics (e.g., tetracycline-inducible promoters), and those regulated by metal ions (e.g., metallothionein-1 promoters), steroid hormones, small molecules (e.g., alcohol-regulated promoters), heat shock, and the like. Non-limiting examples of tissue specific promoters include B29 promoter, CD14 promoter, CD43 promoter, CD45 promoter, CD68 promoter, desmin promoter, elastase-1 promoter, endoglin promoter, fibronectin promoter, Flt-1 promoter, GFAP promoter, GPIIb promoter, ICAM-2 promoter, INF-β promoter, Mb promoter, Nphsl promoter, OG-2 promoter, SP-B promoter, SYN1 promoter, and WASP promoter. The promoter sequence can be wild type or it can be modified for more efficient or efficacious expression.

In alternate embodiments, the sequence encoding the fusion protein can be operably linked to at least one promoter control sequence for expression in bacterial or eukaryotic cells such that the fusion protein can be isolated and/or purified. Thus, the fusion protein can be introduced into the cell of interest as an isolated protein. Suitable bacterial promoters include, without limit, T7 promoters, lac operon promoters, trp promoters, variations thereof, and combinations thereof. An exemplary bacterial promoter is tac which is a hybrid of trp and lac promoters. Non-limiting examples of suitable eukaryotic promoters are listed above.

In some embodiments, the nucleic acid encoding the fusion protein can be present in a vector. Suitable vectors include plasmid vectors, phagemids, cosmids, artificial/mini-chromosomes, transposons, and viral vectors. In an exemplary embodiment, the nucleic acid encoding the fusion protein is DNA which is present in a plasmid vector. Non-limiting examples of suitable plasmid vectors include pUC, pBR322, pET, pBluescript, and variants thereof. The vector can comprise additional expression control sequences (e.g., enhancer sequences, Kozak sequences, polyadenylation sequences, transcriptional termination sequences, etc.), selectable marker sequences (e.g., antibiotic resistance genes), origins of replication, and the like. Additional information can be found in "Current Protocols in Molecular Biology" Ausubel et al., John Wiley & Sons, New York, 2003 or "Molecular Cloning: A Laboratory Manual" Sambrook & Russell, Cold Spring Harbor Press, Cold Spring Harbor, N.Y., 3rd edition, 2001.

(III) Method for Targeted Histone Acetylation

A further aspect of the disclosure provides a method for acetylating at least one histone protein at a targeted chromosomal location in a cell. The method comprises contacting the cell with a fusion protein or a nucleic acid encoding the fusion protein, wherein the fusion protein comprises a DNA binding domain and at least one HAT domain. Upon binding of the DNA binding domain of the fusion protein to a specific sequence at the targeted chromosomal location, the HAT domain of the fusion protein acetylates at least one histone protein at the targeted chromosomal location.

(a) Contact with the Fusion Protein

The method comprises contact with an isolated fusion protein or a nucleic acid encoding the fusion protein. Fusion proteins are detailed above in section (I) and nucleic acids encoding the fusion proteins are described above in section (II).

The fusion protein or nucleic acid encoding the fusion protein can be introduced into the cell by a variety of means. Suitable delivery means include microinjection, electroporation, sonoporation, biolistics, calcium phosphate-mediated transfection, cationic transfection, liposome transfection, dendrimer transfection, heat shock transfection, nucleofection transfection, magnetofection, lipofection, impalefection, optical transfection, proprietary agent-enhanced uptake of nucleic acids, and delivery via liposomes, immunoliposomes, virosomes, or artificial virions. In a specific embodiment, the fusion protein or nucleic acid encoding the fusion protein are introduced into the cell by nucleofection.

In general, the cell is maintained under conditions appropriate for cell growth and/or maintenance. Suitable cell culture conditions are well known in the art and are described, for example, in Santiago et al. (2008) PNAS 105:5809-5814; Moehle et al. (2007) PNAS 104:3055-3060; Urnov et al. (2005) Nature 435:646-651; and Lombardo et al (2007) Nat. Biotechnology 25:1298-1306. Those of skill in the art appreciate that methods for culturing cells are known in the art and can and will vary depending on the cell type. Routine optimization may be used, in all cases, to determine the best techniques for a particular cell type.

Upon binding of the DNA binding domain of the fusion protein to the targeted sequence, the HAT domain of the fusion protein acetylates at least one histone protein at the targeted sequence. The histone protein in which at least one lysine residue is acetylated can be one or more of the core histones (i.e., H2A, H2B, H3, or H4). In one embodiment, the fusion protein acetylates at least one lysine residue of histone H3. Exemplary lysine (K) residues in histone H3 include K4, K9, K14, K18, K23, K27, K42, and K56. In exemplary embodiments, the fusion protein acetylates lysine 18 and lysine 27 of histone H3. The degree of acetylation on a specific lysine residue in the histone protein can be increased by about 1.2-fold, 1.5-fold, 2-fold, 2.5-fold, 3-fold, 3.5-fold, 4-fold, 4.5-fold, 5-fold, 6-fold, 7-fold, 8-fold, 9-fold, 10-fold, or more than 10-fold. Persons skilled in the art are familiar with means for determining acetylation levels of histone proteins (see, e.g., Example 1).

In general, the increased histone acetylation results in increased transcription of the targeted chromosomal sequence. Transcription may be increased about 1.5-fold, 2-fold, 3-fold, 4-fold, 5-fold, 6-fold, 7-fold, 8-fold, 9-fold, 10-fold, 12-fold, 14-fold, 16-fold, 18-fold, 20-fold, 22-fold, 24-fold, 26-fold, 28-fold, 30-fold, 35-fold, 40-fold, 45-fold, 50-fold, 60-fold, 80-fold, 100-fold, or more than 100-fold. Suitable means for measuring the levels of expression are well known in the art (see, e.g., Example 2).

(b) Cell Types

A variety of cells are suitable for use in the method. In various embodiments, the cell can be a human cell, a non-human mammalian cell, a non-mammalian vertebrate cell, an invertebrate cell, an insect cell, a plant cell, a yeast cell, or a single cell eukaryotic organism. A variety of embryos are suitable for use in the method. For example, the embryo can be a one cell non-human mammalian embryo. Exemplary mammalian embryos, including one cell embryos, include without limit mouse, rat, hamster, rodent, rabbit, feline, canine, ovine, porcine, bovine, equine, and primate embryos. In still other embodiments, the cell can be a stem cell. Suitable stem cells include without limit embryonic stem cells, ES-like stem cells, fetal stem cells, adult stem cells, pluripotent stem cells, induced pluripotent stem cells, multipotent stem cells, oligopotent stem cells, unipotent stem cells and others. In exemplary embodiments, the cell is a mammalian cell.

Non-limiting examples of suitable mammalian cells include human embryonic kidney cells (HEK293, HEK293T); human K562 cells; human cervical carcinoma cells (HELA); human lung cells (W138); human liver cells (Hep G2); human U2-OS osteosarcoma cells, human A549 cells, human A-431 cells; monkey kidney SV-40 transformed fibroblast (COS7) cells; monkey kidney CVI-76 cells; African green monkey kidney (VERO-76) cells; Chinese hamster ovary (CHO) cells, baby hamster kidney (BHK) cells; mouse myeloma NSO cells, mouse embryonic fibroblast 3T3 cells (NIH3T3), mouse B lymphoma A20 cells; mouse melanoma B16 cells; mouse myoblast C2C12 cells; mouse myeloma SP2/0 cells; mouse embryonic mesenchymal C3H-10T½ cells; mouse carcinoma CT26 cells, mouse prostate DuCuP cells; mouse breast EMT6 cells; mouse hepatoma Nepal c1c7 cells; mouse myeloma J5582 cells; mouse epithelial MTD-1A cells; mouse myocardial MyEnd cells; mouse renal RenCa cells; mouse pancreatic RIN-5F cells; mouse melanoma X64 cells; mouse lymphoma YAC-1 cells; rat glioblastoma 9L cells; rat B lymphoma RBL cells; rat neuroblastoma B35 cells; rat hepatoma cells (HTC); buffalo rat liver BRL 3A cells; canine kidney cells (MDCK); canine mammary (CMT) cells; rat osteosarcoma D17 cells; and rat monocyte/macrophage DH82 cells. An extensive list of mammalian cell lines may be found in the American Type Culture Collection catalog (ATCC, Mamassas, Va.).

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

The term "DNA binding domain" refers to a protein domain comprising at least one motif that recognizes and binds a specific DNA sequence.

The term "gene," as used herein, refers to a DNA region (including exons and introns) encoding a gene product, as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites, and locus control regions.

The term "HAT domain" refers to a protein domain or functional variant thereof that exhibits histone acetylase activity.

The term "nucleic acid" refers to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analog of A will base-pair with T or an analog of T.

The terms "protein" and "polypeptide" are used interchangeably to refer to a polymer of amino acid residues.

The terms "upstream" and "downstream" refer to locations in a nucleic acid sequences relative to a fixed position. As used herein, "upstream" refers to the locations 5' to the transcriptional start site of a gene and are given negative numbers (e.g., −100 bp, −500 bp, etc.), and "downstrream" refers to the locations 3' to the transcriptional start site of a gene and are given positive numbers (e.g., +100 bp, +500 bp, etc.).

EXAMPLES

The following examples are included to illustrate, but not to limit the claimed invention.

Example 1. ZF(Oct4)-p300 Fusion Protein Acetylated Histones Associated with Oct4 Gene A fusion protein was designed to target a specific sequence near the transcriptional start site of the human OCT4 gene. The fusion protein contained a zinc finger (ZF) DNA binding domain and a HAT domain derived from human E1A binding protein p300 (i.e., p300 HAT domain). The ZF binding domain was designed to bind the specific sequence 5'-GGAGGGcCAGGAATCGGGC-3' (SEQ ID NO:1) starting at nucleotide +181 downstream from the transcriptional start site of OCT4. This ZF DNA binding domain, termed ZF(Oct4+181), had the following amino acid sequence:

AAMAERPFQCRICMRNFSDRSHLTRHIRTHTGEKPFACDICGRKFARNDDRKKHTKIH TGSQKPFQCRICMRNFSQSGNLARHIRTHTGEKPFACDICGRKFAAKWNLDAHTKIHT HPRAPIPKPFQCRICMRNFSRSAHLSRHIRTHTGEKPFACDICGRKFAQSGHLSRHTKI HLRQKDAAR (SEQ ID NO:2). The HAT domain corresponded to amino acids 1284-1673 of human E1A binding protein p300 (accession number: NM_001429). Amino acids 1284-1673 are in bold in the sequence of human E1A binding protein p300 presented below:

MAENVVEPGPPSAKRPKLSSPALSASASDGTDFGSLFDLEHDLPDELINSTELGLTNGGDINQL QTSLGMVQDAASKHKQLSELLRSGSSPNLNMGVGGPGQVMASQAQQSSPGLGLINSMVKSPMTQ AGLTSPNMGMGTSGPNQGPTQSTGMMNSPVNQPAMGMNTGMNAGMNPGMLAAGNGQGIMPNQVM NGSIGAGRGRQNMQYPNPGMGSAGNLLTEPLQQGSPQMGGQTGLRGPQPLKMGMMNNPNPYGSP YTQNPGQQIGASGLGLQIQTKTVLSNNLSPFAMDKKAVPGGGMPNMGQQPAPQVQQPGLVTPVA QGMGSGAHTADPEKRKLIQQQLVLLLHAHKCQRREQANGEVRQCNLPHCRTMKNVLNHMTHCQS GKSCQVAHCASSRQIISHWKNCTRHDCPVCLPLKNAGDKRNQQPILTGAPVGLGNPSSLGVGQQ SAPNLSTVSQIDPSSIERAYAALGLPYQVNQMPTQPQVQAKNQQNQQPGQSPQGMRPMSNMSAS PMGVNGGVGVQTPSLLSDSMLHSAINSQNPMMSENASVPSLGPMPTAAQPSTTGIRKQWHEDIT QDLRNHLVHKLVQAIFPTPDPAALKDRRMENLVAYARKVEGDMYESANNRAEYYHLLAEKIYKI QKELEEKRRTRLQKQNMLPNAAGMVPVSMNPGPNMGQPQPGMTSNGPLPDPSMIRGSVPNQMMP RITPQSGLNQFGQMSMAQPPIVPRQTPPLQHHGQLAQPGALNPPMGYGPRMQQPSNQGQFLPQT QFPSQGMNVTNIPLAPSSGQAPVSQAQMSSSSCPVNSPIMPPGSQGSHIHCPQLPQPALHQNSP SPVPSRTPTPHHTPPSIGAQQPPATTIPAPVPTPPAMPPGPQSQALHPPPRQTPTPPTTQLPQQ VQPSLPAAPSADQPQQQPRSQQSTAASVPTPTAPLLPPQPATPLSQPAVSIEGQVSNPPSTSST EVNSQAIAEKQPSQEVKMEAKMEVDQPEPADTQPEDISESKVEDCKMESTETEEERSTELKTEIK EEEDQPSTSATQSSPAPGQSKKKIFKPEELRQALMPTLEALYRQDPESLPFRQPVDPQLLGIPD YFDIVKSPMDLSTIKRKLDTGQYQEPWQYVDDIWLMFNNAWLYNRKTSRVYKYCSKLSEVFEQE IDPVMQSLGYCCGRKLEFSPQTLCCYGKQLCTIPRDATYYSYQNRYHFCEKCFNEIQGESVSLG DDPSQPQTTINKEQFSKRKNDTLDPELFVECTECGRKMHQICVLHHEIIWPAGFVCDGCLKKSA RTRKENKFSAKRLPSTRLGTFLENRVNDFLRRQNHPESGEVTVRVVHASDKTVEVKPGMKARFV DSGEMAESFPYRTKALFAFEEIDGVDLCFFGMHVQEYGSDCPPPNQRRVYISYLDSVHFFRPKC LRTAVYHEILIGYLEYVKKLGYTTGHIWACPPSEGDDYIFHCHPPDQKIPKPKRLQEWYKKMLD KAVSERIVHDYKDIFKQATEDRLTSAKELPYFEGDFWPNVLEESIKELEQEEEERKREENTSNE STDVTKGDSKNAKKKNNKKTSKNKSSLSRGNKKKPGMPNVSNDLSQKLYATMEKHKEVFFVIRL IAGPAANSLPPIVDPDPLIPCDLMDGRDAFLTLARDKHLEFSSLRRAQWSTMCMLVELHTQSQD RFVYTCNECKHHVETRWHCTVCEDYDLCITCYNTKNHDHKMEKLGLGLDDESNNQQAAATQSPG DSRRLSIQRCIQSLVHACQCRNANCSLPSCQKMKRV-VQHTKGCKRKTNGGCPICKQLIALCCYH AKHCQENKCPVPFCLNIKQKLRQQQLQHRLQQAQMLRRRMASMQRTGVVGQQQGLPSPTPATPT TPTGQQPTTPQTPQPTSQPQPTPPNSMPPYLPRTQAAGPVSQGKAAGQ VTPPTPPQTAQPPLPG PPPAAVEMAMQIQRAAETQRQMAHVQIFQRPIQHQMPPMTPMAPMGMNPPPMTRGPSGHLEPGM GPTGMQQQPPWSQGGLPQPQQLQSGMPRPAMMSVAQHGQPLNMAPQPGL GQVGISPLKPGTVSQ QALQNLLRTLRSPSSPLQQQQVLSILHANPQLLAAFIKQRAAKYANSNPQPIPGQPGMPQGQPG LQPPIMPGQQGVHSNPAMQNMNPMQAGVQRAGLPQQQPQQQLQPPMGG MSPQAQQMNMNHNIMP SQFRDILRRQQMMQQQQQQGAGPGIGPGMANHNQFQQPQGVGYPPQQQQRMQHHMQQMQQGNMG QIGQLPQALGAEAGASLQAYQQRLLQQQMGSPVQPNPMSPQQHMLPN QAQSPHLQGGQIPNSLS NQVRSPQPVPSPRPQSQPPHSSPSPRMQPQPSPHHVSPQTSSPHPGLVAAQANPMEQGHFASPD QNSMLSQLASNPGMANLHGASATDLGLSTDNSDLNSNLS QSTLDIH (SEQ ID NO:13).

An expression vector encoding the fusion protein ZF(Oct4+181)-p300 was transfected into HEK 293 cells. Negative control cells were transfected with vectors encoding GFP or the p300 HAT domain (without the ZF). Cells treated with sodium butyrate (Nabut), a histone deacetylase inhibitor, were used as positive controls. Histone acetylation of histone H3 Lys18 (H3K18) and histone H3 Lys27 (H3K27) at the Oct4 promoter site were analyzed and compared at 48 hrs post-transfection/treatment. Cells were cross-linked and chromatin was sonicated per the technical bulletin of Imprint™ Chromatin Immunoprecipitation Kit (Sigma Aldrich, St. Louis, Mo.). Antibodies used for ChIP studies were α-H3K18ac and α-H3K27ac (Abcam, Cambridge, Mass.). Quantitative PCR was performed with SYBR Green. Primers specific for the control "ZF target site" were 5'-GAAGATGGGGTGAAATTTGGC-3' (SEQ ID NO:3) and 5'-TGGCACTCTCTCAGGCTCTG-3' (SEQ ID NO:4), and primers specific for the "ZF target site +200 bp" (i.e., oct4+181) were 5'-CGGCTTGGAGACCTCTCAG-3' (SEQ ID NO:5) and 5'-CCAGCTTCACGGCACCAG'3' (SEQ ID NO:6). FIG. 1 illustrates that the fusion protein ZF(Oct4+181)-p300 increased acetylation of both H3K18 and H3K27.

Example 2. ZF(Oct4+181)-p300 Fusion Protein Increased Oct4 Expression

Additional ZF-p300 HAT domain fusion proteins were designed that targeted sequences located at nucleotides −720 or −615 upstream of the transcriptional start site of OCT4: ZF(Oct4-720)-p300 and ZF(Oct4-615)-p300. A second set of control fusion proteins containing NF-κB subunit p65 was also constructed to use as positive controls: ZF(Oct4+181)-p65 and ZF(Oct4-720)-p65.

Figure 2:
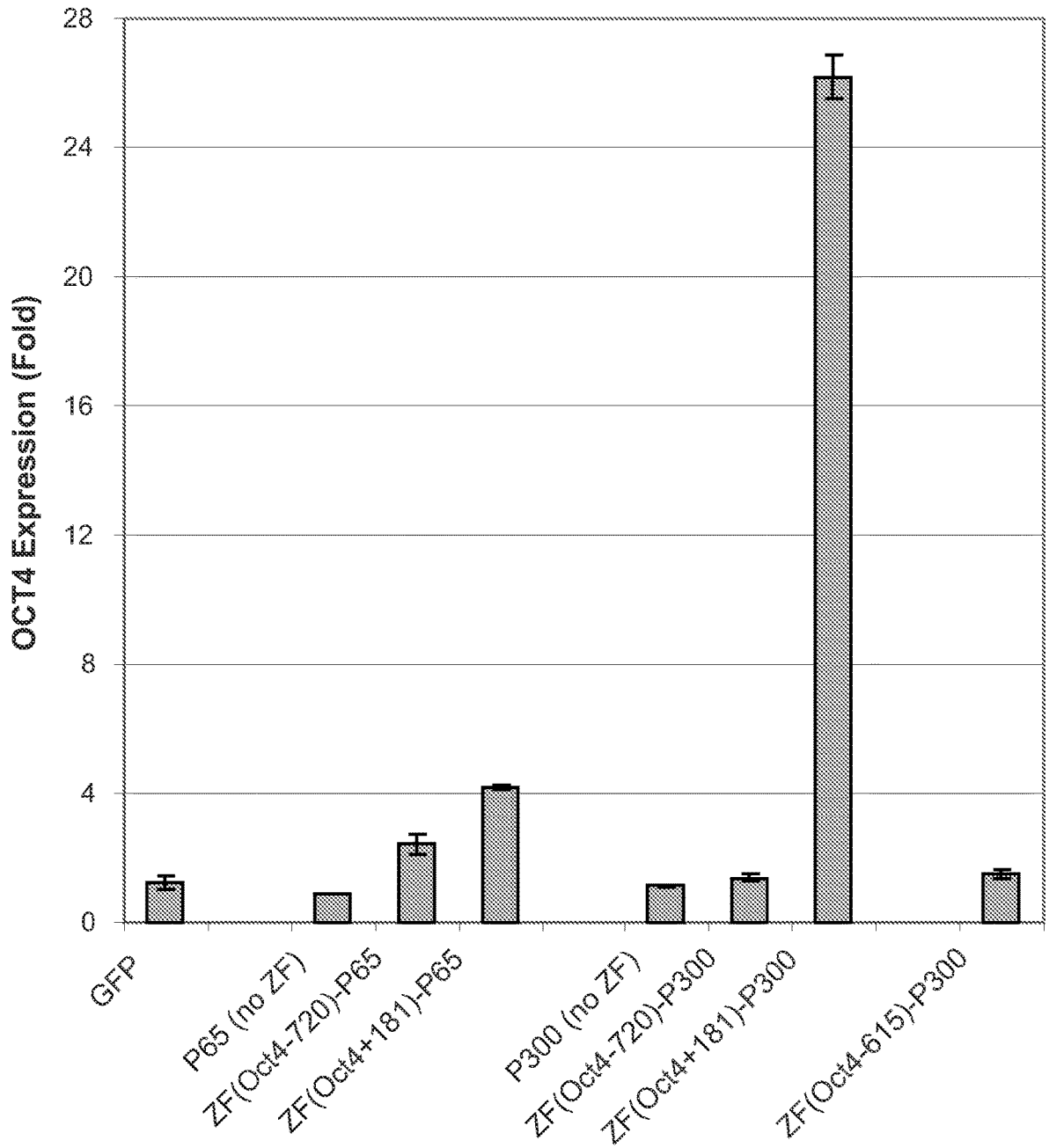
FIG. 2 depicts activation of Oct4 expression in HEK293 cells by the fusion protein ZF(Oct4+181)-p300. Plotted is the fold increase in OCT4 expression under the indicated treatment conditions. Each bar represents the mean (±SD) of the OCT4/cyclophilin A ratios of triplicate RT-PCRs. Cells expressing ZF-p65 fusion proteins were used as positive controls (p65 is a component of the NF-κ13 transcription factor). Cells expressing only p65, p300, or GFP were used as negative controls. Cells expressing the fusion protein ZF(Oct4+181)-p300 showed marked activation of OCT4 expression (>25-fold) over negative control cells.

Expression vectors encoding ZF(Oct4+181)-p300 or one of the control fusion proteins described above were transfected into HEK 293 cells. Control cells were transfected with vectors encoding GFP, p65 (no ZF), or p300 (no ZF). After 48 hrs, the cells were harvested and total RNA was isolated. The levels of OCT4 mRNA and cyclophilin A (i.e., PPIA) endogenous control mRNA were measured by real time reverse transcriptase polymerase chain reaction (RT-PCR) (Life Technologies, Carlsbad, Calif.). The OCT4/cyc ratio was used for normalizing OCT4 expression. As shown in FIG. 2, the ZF(Oct4+181)-p300 fusion protein also increased OCT4 expression by greater than 25-fold. Thus, increased acetylation of histones associated with the OCT4 gene resulted in increased OCT4 transcription.

Example 3. ZF(PEDF)-p300 Fusion Protein Increased PEDF Expression

To test whether ZF fusion proteins comprising the p300 HAT domain were able to activate other genes, a ZF DNA binding domain fusion was designed to target the human PEDF (pigment epithelium-derived factor) gene. The ZF binding domain was designed to bind the specific sequence 5'-GGATGGtGGTGCAGCAGTG-3' (SEQ ID NO:7) starting at nucleotide −92 upstream from the transcriptional start site of the sequence encoding PEDF. The ZF(PEDF) DNA binding domain was termed ZF6961 and had the following amino acid sequence: AAMAERPFQCRICMRNFSRSDALSRHIRTHTGEKP-FACDICGRKFAQSGDLTRHTKIH TGGGQRPFQCRICM-RNFSQSGDLTRHIRTHTGEKPFACDICGRKFATS-GHLSRHTKIHT GGGGSQKPFQCRICMRNFSRSDHLSNHIRTHTGEKP-FACDICGKKFAQSATRITHTKIH LRQKDAAR (SEQ ID NO:8). The ZF(PEDF) DNA binding domain was linked to either the p300 HAT domain or the NF-κB p65 subunit.

Figure 3:
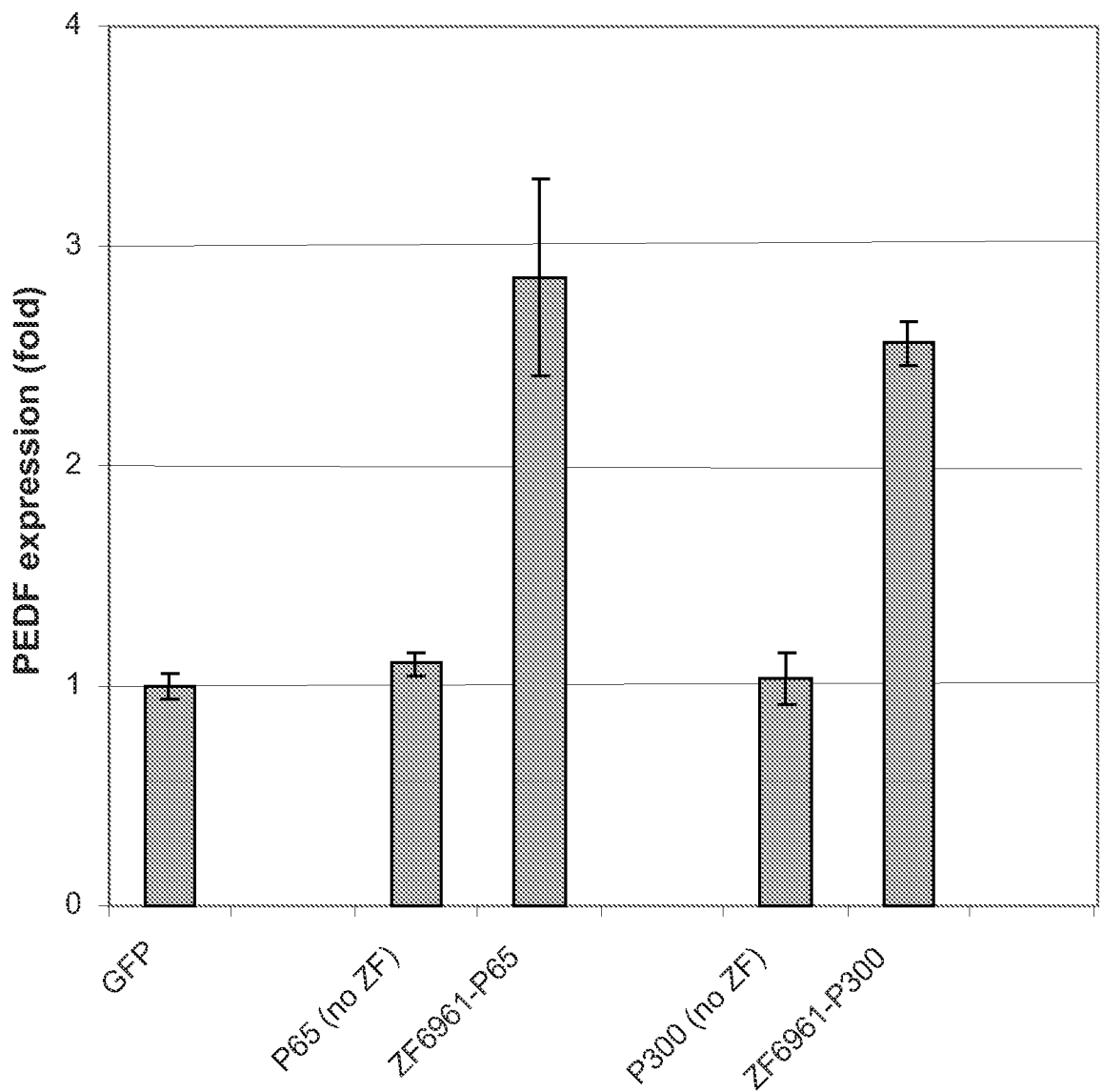
FIG. 3 illustrates activation of PEDF expression in HEK293 cells by the fusion protein ZF(PEDF)-p300. Plotted is the fold increase in PEDF expression under the indicated treatment conditions. Each bar represents the mean (±SD) of the PEDF/cyclophilin A ratios of triplicate RT-PCRs. The DNA binding domain ZF6961 targets the PEDF gene. Cells expressing ZF6961-p65 fusion protein were used as positive controls. Cells expressing only p65, p300, or GFP were used as negative controls. Cells expressing the fusion protein ZF6961-p300 had increased expression of PEDF (P<0.001).

Expression vectors encoding ZF(PEDF)-p300 or ZF(PEDF)-p65 were transfected into HEK 293 cells. Control cells were transfected with vectors encoding GFP, p65 (no ZF), or p300 (no ZF). Total RNA was isolated 72 hours later, and the levels of PEDF mRNA and cyclophilin A endogenous control mRNA were measured by RT-PCR. The PEDF/cyc ratio was used for normalizing PEDF expression. The results are shown in FIG. 3. The fusion protein ZF(PEDF)-p300 increased the expression of PEDF by more than about 2.5-fold.

Example 4. ZF(PEDF)-GCN5 Did not Affect PEDF Expression

Figure 4:
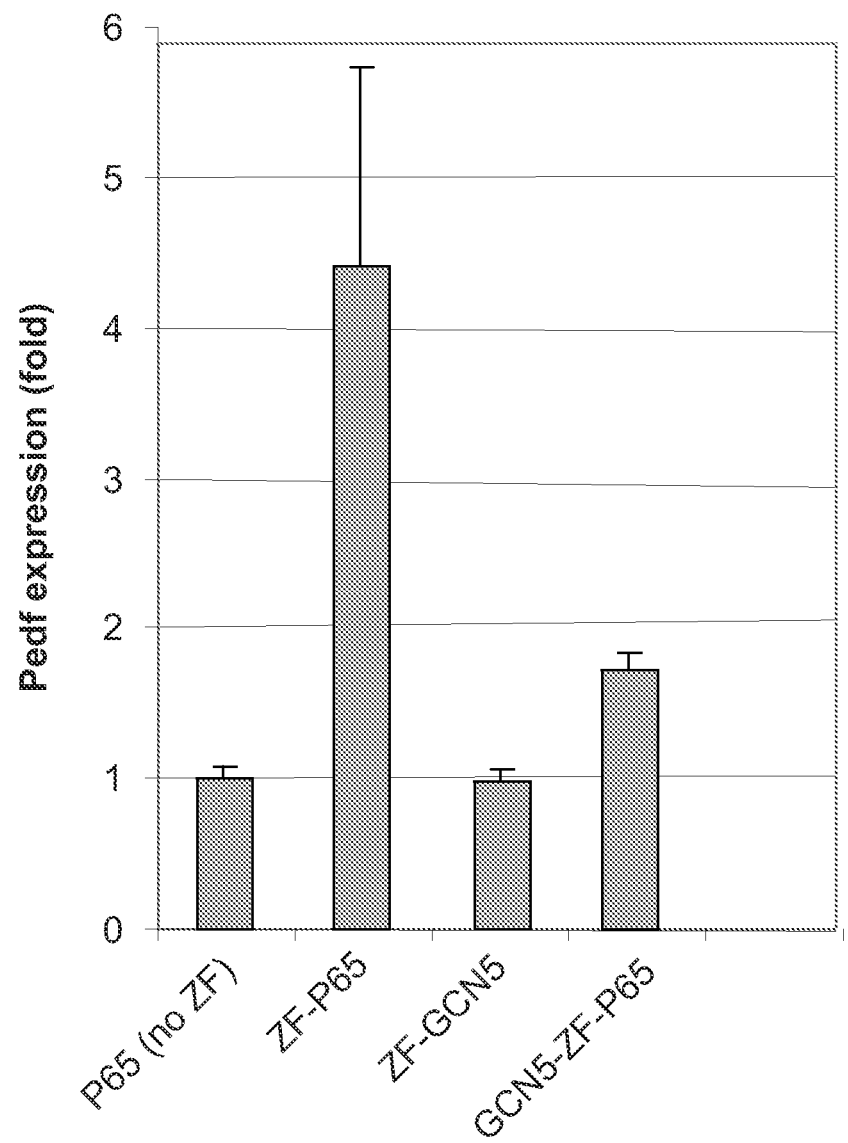
FIG. 4 shows that the fusion protein ZF(PEDF)-GCN5 did not activate PEDF expression in HEK293 cells. Plotted is the fold increase in PEDF expression under the indicated treatment conditions. Each bar represents the mean (±SD) of the PEDF/cyclophilin A ratios of triplicate RT-PCRs. The ZF DNA binding domain targets the PEDF gene. Cells expressing ZF-p65 fusion protein were used as positive controls. Cells expressing only p65 were used as negative controls. Cells expressing the fusion protein ZF-GCN5 did not display an increase in PEDF expression.

To determine whether the HAT domain of another histone acetyltransferase could substitute for p300, a set of fusion proteins containing the HAT domain of GCN5 was constructed. The HAT domain corresponded to amino acids 491-662 of human GCN5 (accession number: NM_021078). The HAT domain of CGN5 was linked to either ZF(PEDF) to create ZF-GCN5 or to ZF(PEDF)-p65 to create GCN5-ZF-p65. Cells were transfected with vectors expressing ZF-p65 (i.e., ZF(PEDF)-p65), ZF-GCN5), or GCN5-ZF-p65. Control cells were transfected with a vector encoding p65 (no ZF). Total RNA was isolated 72 hours later, and the levels of PEDF mRNA and cyclophilin A endogenous control mRNA were measured by RT-PCR. The PEDF/cyc ratio was used for normalizing PEDF expression. As shown in FIG. 4, ZF-GCN5 did not activate expression of PEDF. In fact, activation by ZF-p65 was weakened by fusion with GCN5.

Example 5. Screening to Optimize ZF(Oct4)-p300 Fusion Proteins

A series of ZF-p300 HAT domain fusion proteins was designed to systematically target sequences around the transcriptional start site of OCT4. ZF domains were designed and constructed using standard procedures to target sequences located from about −2.5 kb upstream to about +1.5 kb downstream of the transcriptional start site of the human OCT4 gene. Expression vectors encoding each ZF(Oct4)-p300 fusion were transfected into HEK 293 cells. Negative control cells were transfected with vectors encoding GFP or the p300 HAT domain (without a ZF domain). The levels of OCT4 mRNA were measured in each population of transfected cells by RT-PCR and OCT4 expression was normalized to cyclophilin A expression essentially as described above in Example 2.

Figure 5:
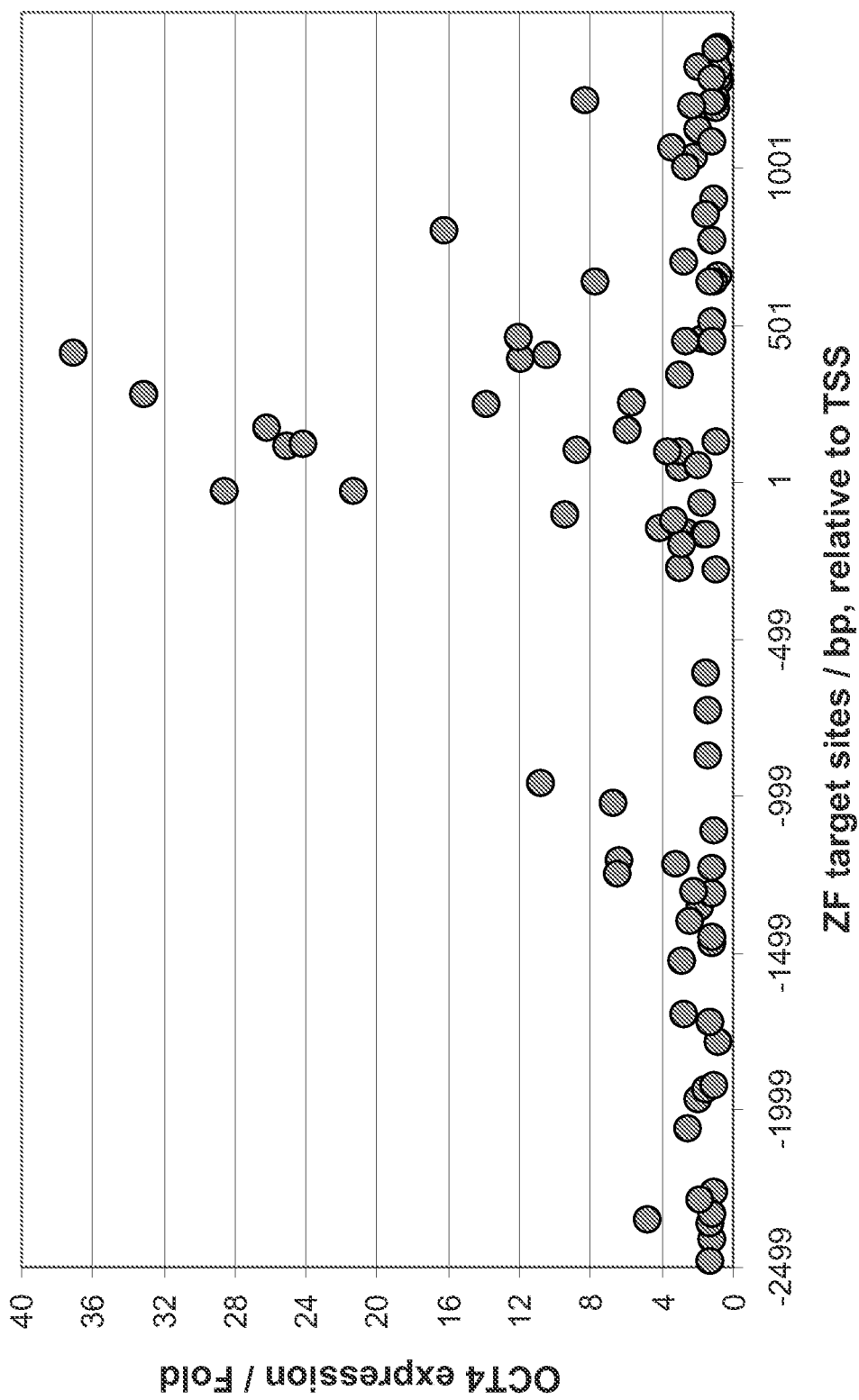
FIG. 5 presents OCT4 expression in the presence of a series of ZF(Oct4)-p300 fusion proteins. Each fusion protein was targeted to a specific sequence located from about −2.5 kb upstream to about 1.5 kb downstream of the transcriptional start site (TSS) of OCT4.

The level of OCT4 expression induced by each of the ZF(Oct4)-p300 fusion proteins is shown in FIG. 5. The fusion proteins that increased OCT4 expression greater than about 20-fold were designed to target sequences located from about −100 bp to about +500 bp of the transcriptional start site.

Example 6. ZF(Oct4)-p300 Fusion Proteins Activated Oct4 Expression and Acetylated Oct4-Associated Histones in Multiple Cell Types Two fusion proteins identified in Example 5 that activated OCT4 expression were tested in other cell types. These proteins were: ZF(Oct4+286)-p300 and ZF(Oct4+420)-p300. The DNA binding domain of ZF(Oct4+286)-p300 had the following amino acid sequence: AAMAERPFQCRICMRNFSRSAHLSRHIRTHTGEKP-FACDICGRKFARSDALARHTKIHT GSQKPFQCRICM-RNFSDRSHLTRHIRTHTGEKPFACDICGRKFATSGSL-TRHTKIHTGS QKPFQCRICMRNFSRSDNLSTHIRTHTGEKP-FACDICGRKFADNRDRIKHTKIHLRQKDAAR (SEQ ID NO:9). The DNA binding domain of ZF(Oct4+420)-p300 had the following amino acid sequence: AAMAERPFQCRICMRNFSQSSNLARHIRTHTGEKP-FACDICGRKFAQSGHLSRHTKIH TGSQKPFQCRICM-RNFSQSSNLARHIRTHTGEKPFACDICGRKFAQS-GHLSRHTKIHT GSQKPFQCRICMRNFSQSSDLSRHIRTHTGEKP-FACDICGRKFAQSGNLARHTKIHLR QKDAAR (SEQ ID NO:10).

Figure 6A:
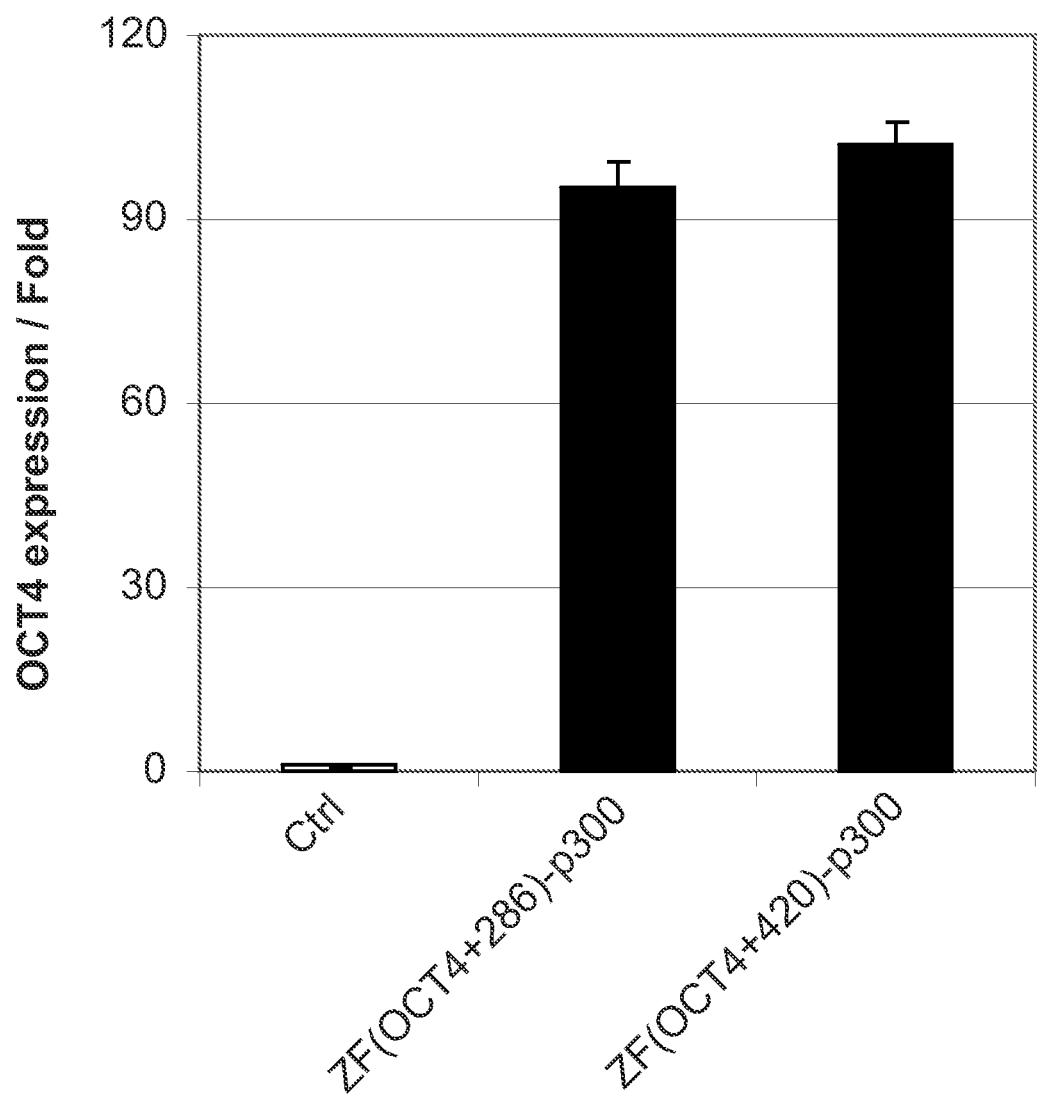
FIG. 6A illustrates that ZF(Oct4)-p300 fusion proteins activated OCT4 expression in HEK293 cells. Plotted in the fold increase in OCT4 expression under control conditions or in the presence of two different fusion proteins targeted downstream sequences.
Figure 6B:
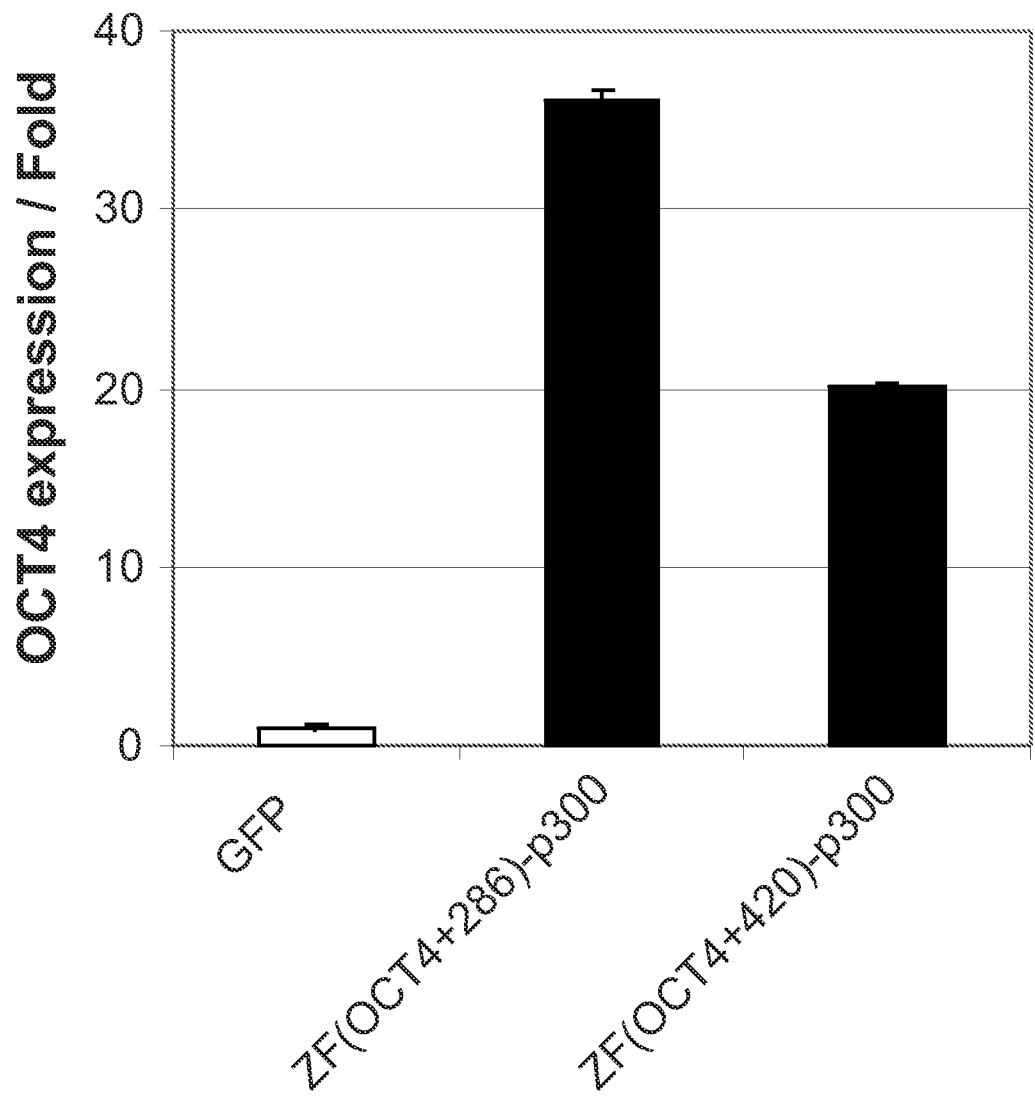
FIG. 6B illustrates that ZF(Oct4)-p300 fusion proteins activated OCT4 expression in K562 cells. Plotted in the fold increase in OCT4 expression under control conditions or in the presence of two different fusion proteins targeted downstream sequences.

HEK293 and K562 cells were transfected with expression vectors encoding each of the fusion proteins, and OCT4 expression was measured as detailed above. As shown in FIG. 6, both fusion proteins increased OCT4 expression in HEK293 cells by at least 90-fold and increased OCT4 expression in K562 cell by at least 20-fold.

Histone acetylation of H3K27 in discrete regions on either side of the transcriptional start site of OCT4 was analyzed by ChIP in both cell types. Cells were harvested 48 hours post-transfection, cross-linked, and chromatin was sonicated as described above in Example 1. Quantitative PCR was performed with SYBR Green using pairs of primers to amplify specific regions (e.g., −1700 bp, −500 bp, −100 bp, +300 bp, +700 bp, +1500 bp, +3000 bp, and +4500 bp). The antibody used for ChIP was α-H3K27ac (Abcam, Cambridge, Mass.).

Figure 7A:
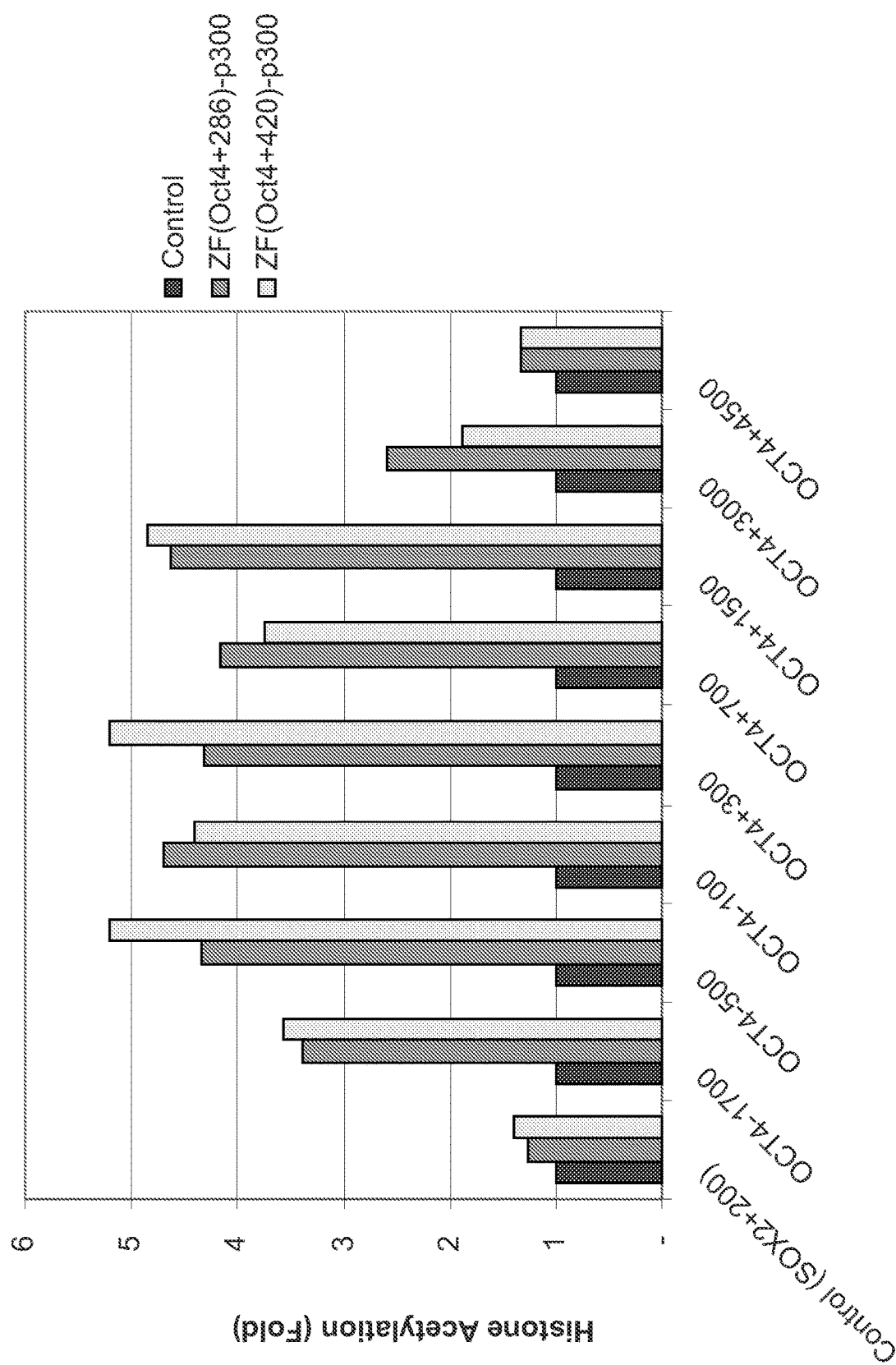
FIG. 7A shows targeted histone acetylation by ZF(Oct4)-p300 fusion proteins in HEK293 cells. Plotted is the fold increase in acetylation at H3K27 at the indicated locations in the absence (control) or presence of ZF(Oct4+286)-p300 or ZF(Oct4+420)-p300 fusion proteins. The control location was +200 downstream of the SOX2 TSS.
Figure 7B:
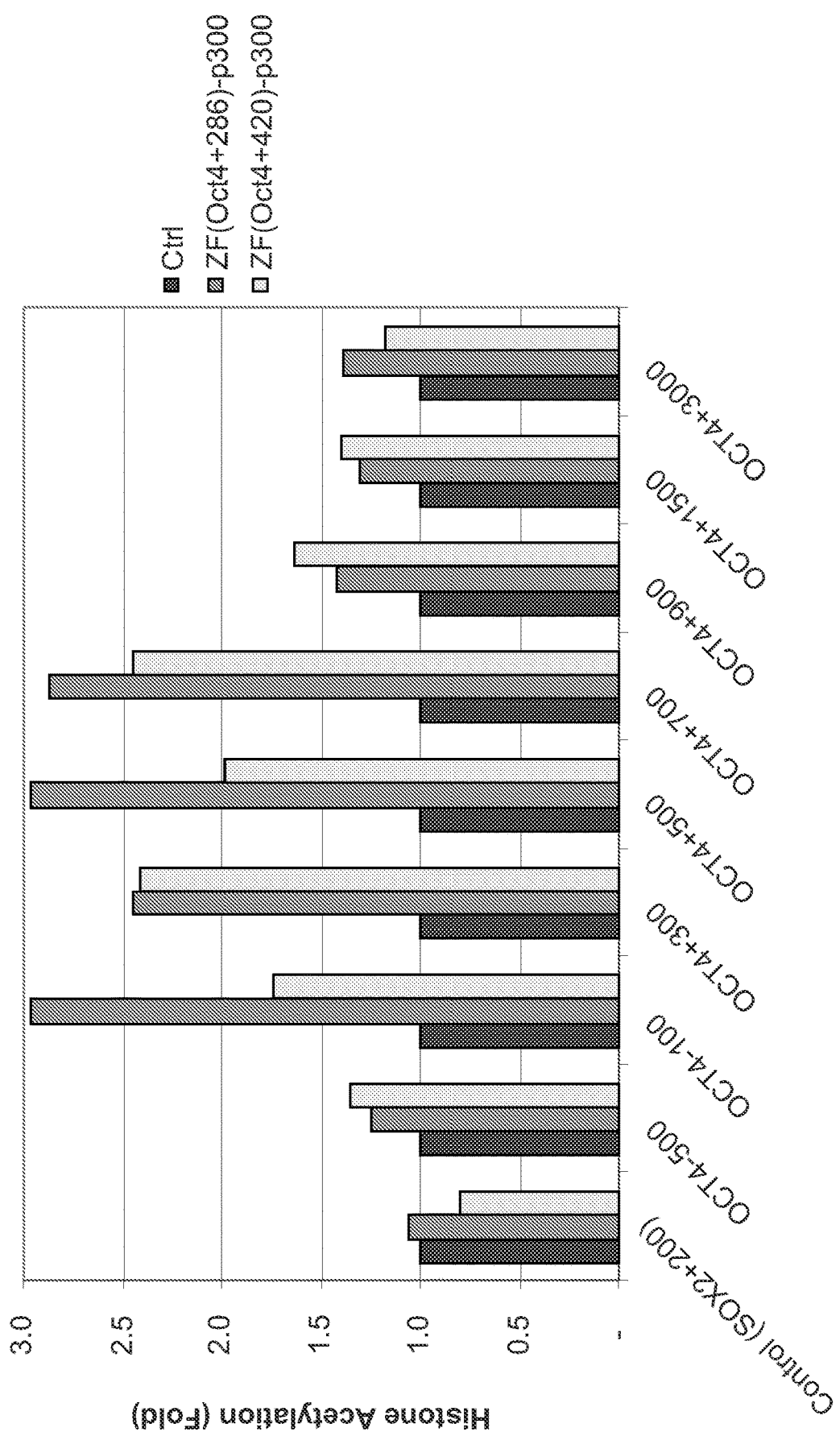
FIG. 7B shows targeted histone acetylation by ZF(Oct4)-p300 fusion proteins in K562 cells. Plotted is the fold increase in acetylation at H3K27 at the indicated locations in the absence (control) or presence of ZF(Oct4+286)-p300 or ZF(Oct4+420)-p300 fusion proteins. The control location was +200 downstream of the SOX2 TSS.

As shown in FIG. 7, ZF(Oct4+286)-p300 and ZF(Oct4+420)-p300 acetylated H3K27 at locations from about −1700 bp to about +3000 bp of the transcriptional start site of OCT4 in HEK293 cells and from about −100 bp to about +900 bp of the transcriptional start site of OCT4 in K562 cells. Thus, the increased acetylation of H3K27 surrounding the start site of OCT4 was associated with increased transcription of the gene.

Example 7. Screening to Identify ZF(Sox2)-p300 Fusion Proteins

A series of ZF-p300 HAT domain fusion proteins was designed to systematically target sequences around the transcriptional start site of SOX2. ZF domains were designed and constructed using standard procedures to target sequences located from about −500 bp upstream to about +1500 bp downstream of the transcriptional start site of the human SOX2 gene. Expression vectors encoding each ZF(Sox2)-p300 fusion were transfected into HEK 293 cells. Negative control cells were transfected with vectors encoding GFP or the p300 HAT domain (without a ZF domain). The levels of SOX2 mRNA were measured by RT-PCR, and SOX2 expression was normalized to cyclophilin A expression in each set of transfected cells.

Figure 8:
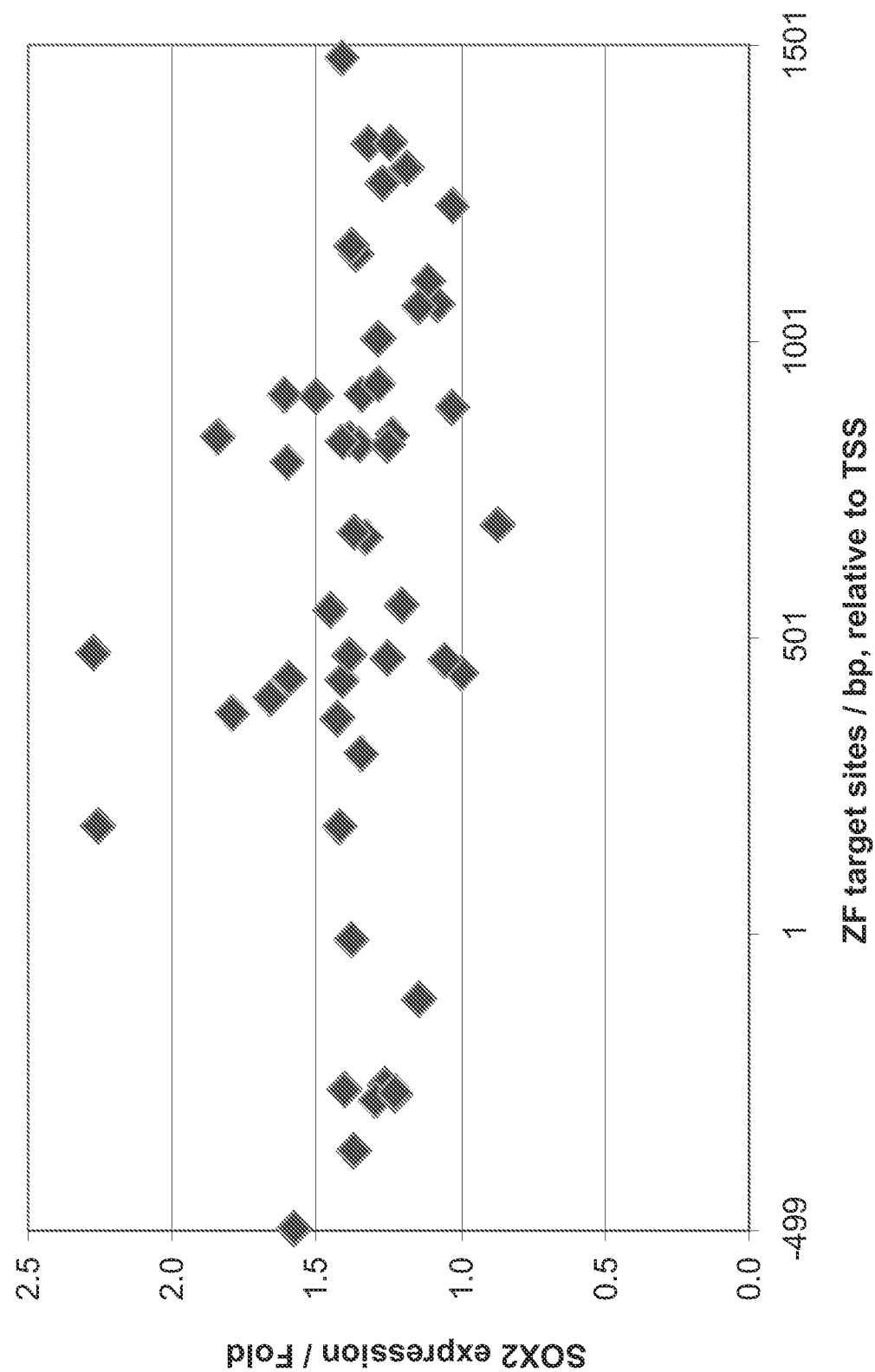
FIG. 8 presents SOX2 expression in the presence of a series of ZF(Sox2)-p300 fusion proteins. Each fusion protein was targeted to a specific sequence located from −0.5 kb upstream to about 1.5 kb downstream of the TSS of SOX2.

The level of SOX2 expression induced by each of the ZF(Sox2)-p300 fusion proteins is shown in FIG. 8. The fusion proteins that increased SOX2 expression the greatest were designed to target sequences located from about −100 bp to about +500 bp of the transcriptional start site.

Two fusion proteins that activated SOX2 expression were tested in other cell types. These proteins were: ZF(Sox2+185)-p300 and ZF(Sox2+r475)-p300 ("r" designates the reverse strand). The DNA binding domain of ZF(Sox2+185)-p300 had the following amino acid sequence:
AAMAERPFQCRICMRNFSRSDDLSKHIRTHTGEKP-FACDICGRKFADRSHLARHTKIH TGSQKPFQCRICM-RNFSQSGDLTRHIRTHTGEKPFACDICGRKFARSDDL-TRHTKIHT GSQKPFQCRICMRNFSRSDDLTRHIRTHTGEKP-FACDICGRKFARNDDRKKHTKIHLR QKDAAR (SEQ ID NO:11). The DNA binding domain of ZF(Sox2+r475)-p300 had the following amino acid sequence:
AAMAERPFQCRICMRNFSRSADLTRHIRTHTGEKP-FACDICGRKFARSDDRKTHTKIH TGSQKPFQCRICM-RNFSDRSHLTRHIRTHTGEKPFACDICGRKFARSDDL-TRHTKIHT GSQKPFQCRICMRNFSQSSDLSRHIRTHTGEKP-FACDICGRKFAYHWYLKKHTKIHLR QKDAAR (SEQ ID NO:12).

Figure 9A:
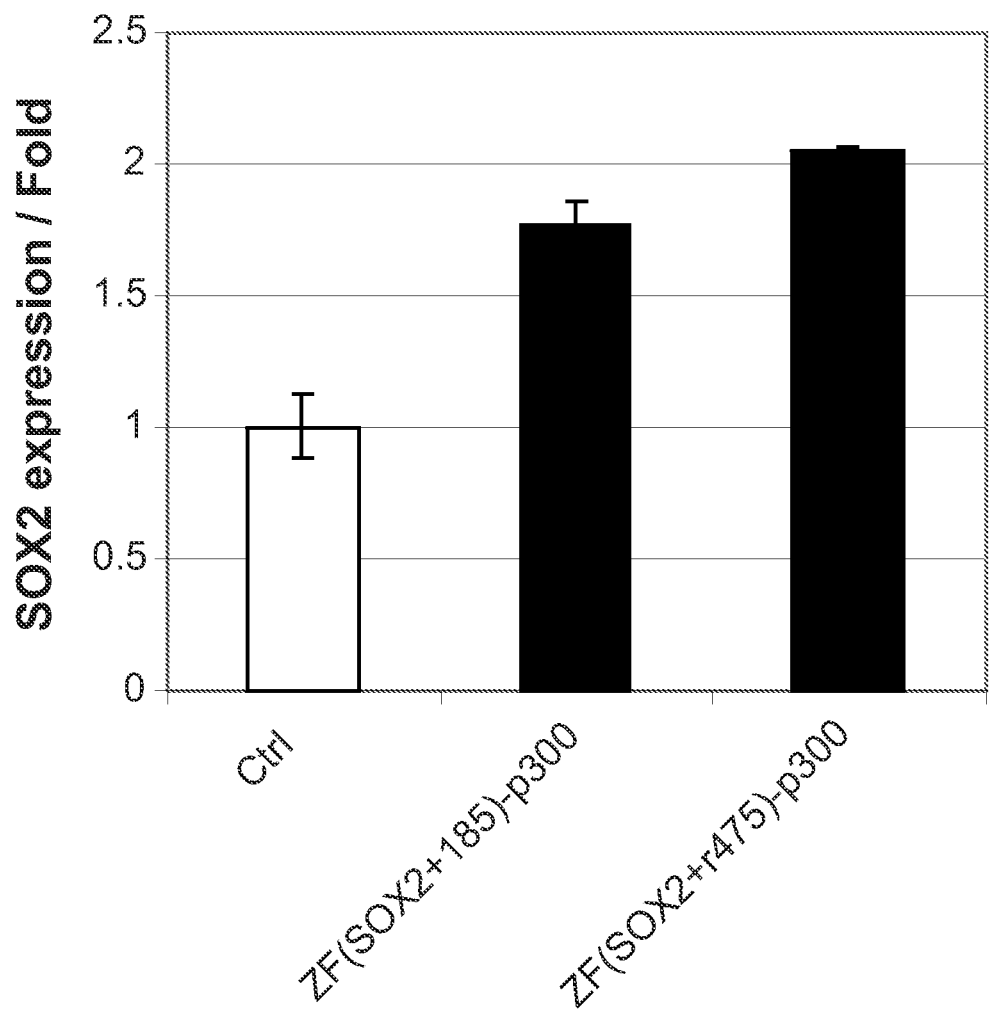
FIG. 9A illustrates that ZF(Sox2)-p300 fusion proteins activated SOX2 expression in HEK293 cells. Plotted is the fold increase in SOX2 expression in under control conditions or in the presence of two different ZF(Sox2)-p300 fusion proteins targeted to downstream sequences.
Figure 9B:
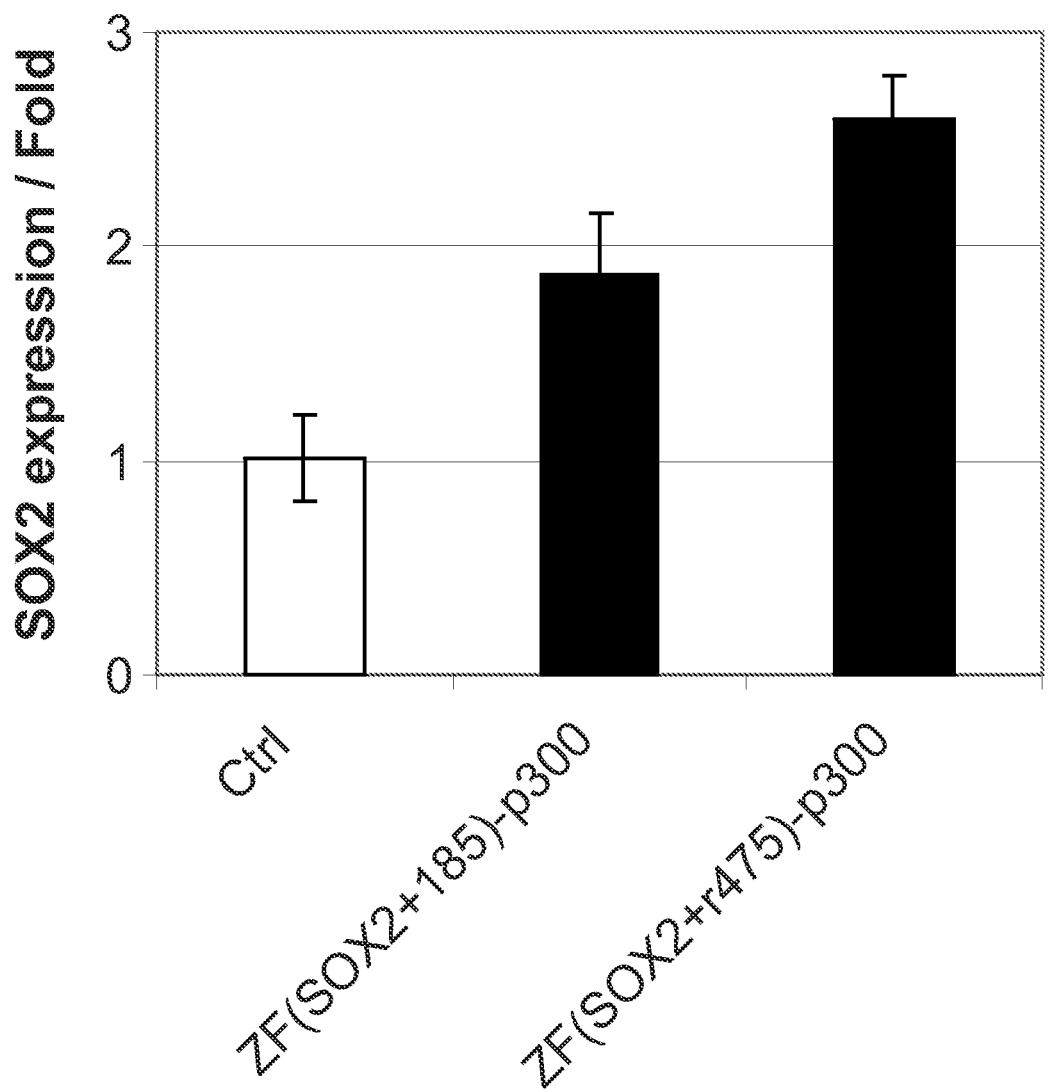
FIG. 9B illustrates that ZF(Sox2)-p300 fusion proteins activated SOX2 expression in K562 cells. Plotted is the fold increase in SOX2 expression under control conditions or in the presence of two different ZF(Sox2)-p300 fusion proteins targeted to downstream sequences.

HEK293 and K562 cells were transfected with expression vectors encoding each of the fusion proteins, and SOX2 expression was measured as detailed above. As shown in FIG. 9, both fusion proteins increased SOX2 expression in HEK293 cells by at least 1.5-fold and increased SOX2 expression in K562 cells by nearly 2-fold or greater.

What is claimed is:

1. A fusion protein comprising a DNA binding domain and a domain having histone acetyltransferase activity that consists essentially of amino acids 1100-1750 of SEQ ID NO:13 or amino acids 1284-1673 of SEQ ID NO:13, wherein the DNA binding domain is a zinc finger DNA binding domain comprising an amino acid sequence selected from the group consisting of SEQ ID NO:2, SEQ ID NO:9 and SEQ ID NO:10.

2. The fusion protein of claim 1, wherein the DNA binding domain further comprises at least one nuclear localization signal, at least one cell-penetrating domain, at least one marker domain, or a combination thereof.

3. An isolated nucleic acid encoding the fusion protein of claim 1.

4. The isolated nucleic acid of claim 3, further comprising at least one expression control sequence.

* * * * *